(12) United States Patent
Merot et al.

(10) Patent No.: US 6,916,787 B2
(45) Date of Patent: Jul. 12, 2005

(54) METHOD FOR PRODUCING HEMIN PROTEINS USING PLANT CELLS, RESULTING PROTEINS AND PRODUCTS CONTAINING SAME

(75) Inventors: Bertrand Merot, Volvic (FR); Wilfrid Dieryck, Saint-Pathus (FR); Philippe Lenee, Noumea (FR); Michael Marden, Aulnay-sous-Bois (FR); Veronique Gruber, Chamalieres (FR); Renee-Josee Pagnier, Le Kremlin-Bicetre (FR); Sylvie Baudino, Orcines (FR); Claude Poyart, Paris (FR)

(73) Assignees: Institut National de la Sante et de Recherche Medicale, Paris Cedex (FR); Meristern Therapeutics, Clermont-Ferrand (FR)

( * ) Notice: Subject to any disclaimer, the term of this patent is extended or adjusted under 35 U.S.C. 154(b) by 108 days.

(21) Appl. No.: 10/085,853

(22) Filed: Oct. 18, 2001

(65) Prior Publication Data

US 2002/0194643 A1 Dec. 19, 2002

Related U.S. Application Data

(62) Division of application No. 08/983,564, filed as application No. PCT/FR96/01123 on Jul. 17, 1996, now Pat. No. 6,344,600.

(30) Foreign Application Priority Data

Jul. 17, 1995 (FR) .............................................. 95 08615

(51) Int. Cl.$^7$ ...................... A61K 38/42; C07K 14/805
(52) U.S. Cl. ........................................ 514/12; 530/385
(58) Field of Search ................................ 530/385, 300, 530/350; 800/278; 435/410, 419, 69.7, 69.1; 514/6.12; 424/185.1

(56) References Cited

U.S. PATENT DOCUMENTS

| | | | |
|---|---|---|---|
| 5,202,422 A | | 4/1993 | Hiatt et al. |
| 5,316,931 A | | 5/1994 | Donson et al. .......... 435/172.3 |
| 5,498,421 A | * | 3/1996 | Grinstaff et al. ............ 424/450 |
| 5,521,154 A | * | 5/1996 | Garlick et al. ................. 514/6 |
| 5,521,853 A | * | 5/1996 | Hibbs et al. ................... 703/1 |
| 5,959,187 A | | 9/1999 | Bailey et al. ............ 800/317.3 |
| 6,344,600 B1 | * | 2/2002 | Merot et al. ................ 800/288 |

FOREIGN PATENT DOCUMENTS

| | | |
|---|---|---|
| EP | 273889 | 7/1988 |
| WO | WO 91/06320 | 5/1991 |
| WO | WO 93/08831 | 5/1993 |
| WO | WO 93/25697 | 12/1993 |
| WO | WO 93/03161 | 2/1998 |

OTHER PUBLICATIONS

Abler, M. et al., "Isolation and characterization of a genomic sequence encoding the mazie Cat3 catalase gene," *Plant Molecular Biology*, vol. 22, pp. 1031–1038 (1993).

Aguilar–Martinez, P. et al., "Comparison of the protein and DNA approaches for the characterization of a β–globin chain variant, hemoglobin Cocody [β$_{21}$ (B3) Asp– → Asn], in a Caucasian patient," *Ann Hematol*, vol. 66, pp. 269–272 (1993).

Efstratiadis, A. et al., "The Structure and Evolution of the Human β–Globin Gene Family," *Cell*, vol. 21, pp. 653–668 (Oct. 1980).

Hardiest, S. et al., "Evolution of the Mammalian β–Globin Gene Cluster," *The Journal of Biological Chemistry*, vol. 259, No. 6, pp. 3748–3756 (Issue of Mar. 25, 1984).

Hardison, R. et al., "Use of Long Sequence Alignments to Study the Evolution and Regulation of Mammalian Globin Gene Clusters," *Mol. Biol. Evol.*, vol. 10, No. 1, pp. 73–102 (1993).

Holm, L. et al., "Structural alignment of globins, phycocyanins and colicin A," *FEBS 11991*, vol. 315, No. 3, pp. 301–306 (1993).

"International Hemoglobin Information Center Variants List," *Hemoglobin*, vol. 19, Nos. 1&2, pp. 39–124 (1995).

Matsunaga, E. et al., "The Rat P450 IID Subfamily: Complete Sequences of Four Closely Linked Genes and Evidence that Gene Conversions Maintained Sequence Homogeneity at the Heme–Binding Region of the Cytochrome P450 Active Site," *J. Mol. Evol.*, vol. 30, pp. 155–169 (1990).

Ni, W. et al., "Characterization of cDNA encoding cottonseed catalase," *Biochimica et Biophysica Acta*, vol. 1049, pp. 219–222 (1990).

Rodriguez Maranon, M. et al., "Analysis of the optical absorption and magnetic–circular–dichroism spectra of peanut peroxidase: electronic structure of a peroxidase with biochemical properties similar to those of horseradish peroxidase," *Biochem. J.*, vol. 301, pp. 335–341 (1994).

Shaanan, B., "Portrait of an Allosteric Protein," *Biochemistry Ed. Steyer*, 4th Edition, W.H. Freeman & Co., New York, Chapter 7, pp. 147–180 (1983).

(Continued)

Primary Examiner—Robert A. Wax
(74) Attorney, Agent, or Firm—Merchant & Gould P.C.

(57) ABSTRACT

A method for producing haemin proteins by (i) inserting into plant cells one or more nucleic acid molecules that each comprise at least one sequence coding for a protein component of an animal haemin protein capable of reversibly binding oxygen, or for a variant or portion of said protein component, and optionally a sequence coding for a selection agent; (ii) selecting cells containing nucleic acid coding for the protein component of the haemin protein; (iii) optionally propagating the transformed cells either in a culture or by regenerating whole transgenic or chimeric plants; and (iv) recovering and optionally purifying a haemin protein that includes a complex consisting of the protein or proteins coded for by said nucleic acid and at least one iron-containing porphyritic nucleus, or a plurality of such complexes.

19 Claims, 11 Drawing Sheets

OTHER PUBLICATIONS

Figure 1:
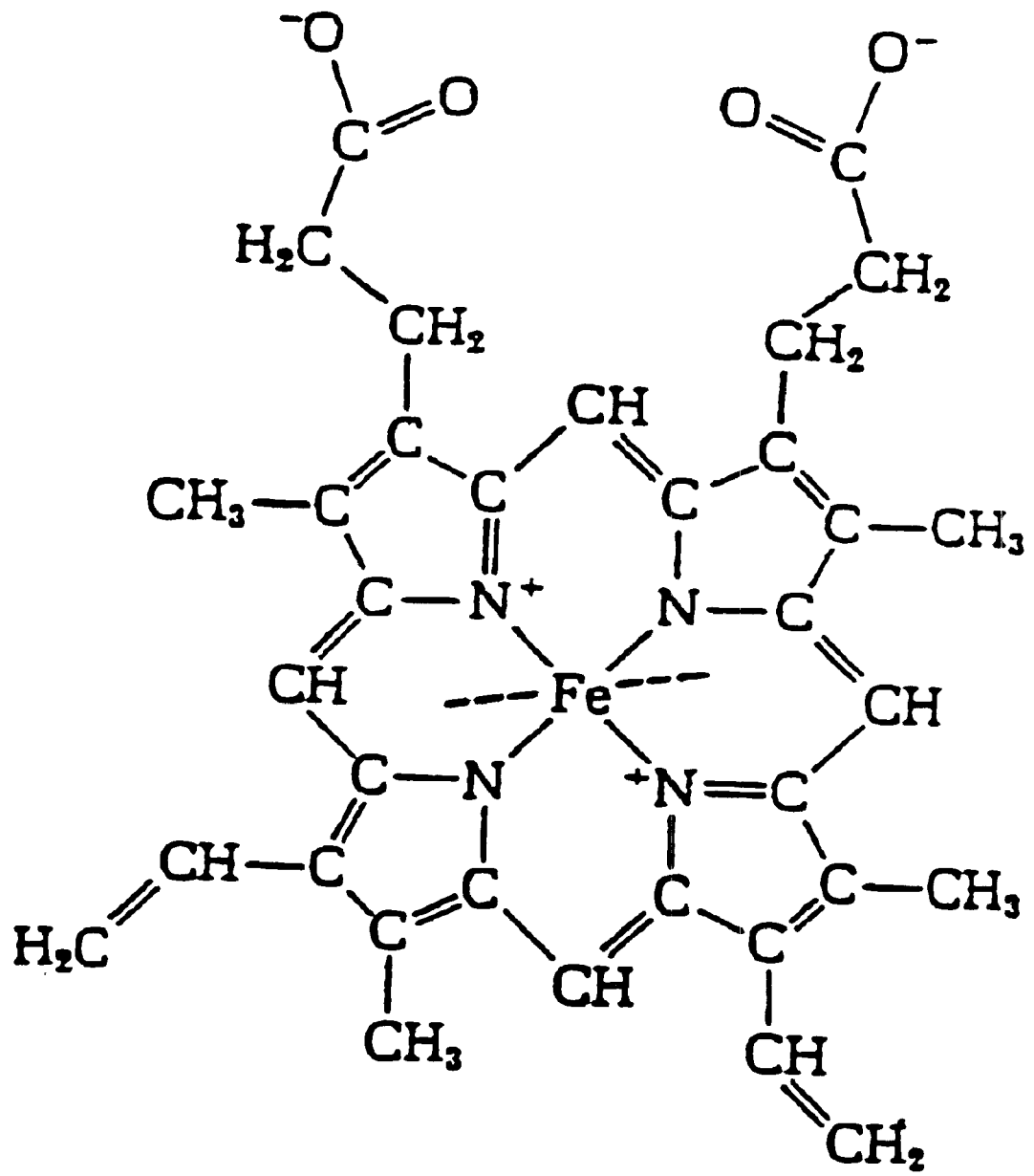

Sheta, E. et al., "Evidence for a Bidomain Structure of Constitutive Cerebellar Nitric Oxide Synthase," *The Journal of Biological Chemistry*, vol. 269, No. 21, pp. 15147–15153 (May 27, 1994).

Souček, P. et al., "Identification of a Common Cytochrome P450 Epitope near the Conserved Heme–Binding Peptide with Antibodies Raised against Recombinant Cytochrome P450 Family 2 Proteins," *Biochemistry*, vol. 34, pp. 16013–16021 (1995).

Vainshtein, B. et al., "Three–dimensional structure of the enzyme catalase," *Nature*, vol. 293, pp. 411–412 (Oct. 1981).

Watts, R, et al., "A hemoglobin from plants homologous to truncated hemoglobins of microorganisms," *PNAS*, vol. 98, No. 18, pp. 10119–10124 (Aug. 28, 2001).

Welinder, K., "Bacterial catalase–peroxidases are gene duplicated members of the plant peroxidase superfamily," *Biochimica et Biophysica Acta*, vol. 1080, pp. 215–220 (1991).

W. Dieryck, V. Gruber, S. Baudino, P. Lenee, J. Pagnier, B. Merot, C. Poyart; "*Recombinant Protein Expression in Plants*"; *Transfusion Cliniqueet Biologique*; 1995; V. 2 No. 6: pp. 441–447.

Masaru Ohme–Takagi, Crispin B. Taylor, Thomas c. Newman, and Pamela J. Green; "*The effect of sequences with high AU content on mRNA stability in tobacco*"; *Proc. Natl. Acad. Sci. USA*; Dec. 1993; vol. 90, pp. 11811–11815.

Michael Wagenbach, Katherine O'Rourke, Laura Vitez, Anna Wieczorek, Stephen Hoffman, Steven Durfee, John Tedesco and Gary Stetler; "*Synthesis of Wild Type and Mutant Human Hemoglobins in Saccaromyces Cerevisiae*"; *Bio/Technology*; Jan. 1991; vol. 9, pp. 57–61.

Aug. 15, 1991 Kazuki Saito, Masaaki Noji, Shigeru Ohmori, Yoshio Imai, and Isamu Murakoshi; "*Integration and expression of a rabbit liver cytochrome P–450 gene in transgenic Nicotiana tabacum*"; *Proceedings of the National Academy of Sciences of the USA*; No. 16, pp. 7041–7045.

R.E. Benesch and S. Kwong: Quantitative Transformation of Hemoglobin into Stable Tetramers; 1994; pp. 185–192.

H.C. Birnboim and J. Doly; "A rapid alkaline extraction procedure for screening recombinant plasmid DNA"; Nucleic Acids Research; 1979; vol. 7, No. 6, 1513–1523.

Marc Boutry and Nam–Hai Chua; "A nuclear gene encoding the beta subunit of the mitochondrial ATP synthase in Nicotiana plumbaginifolia"; *EMBO Journal*; 1985; vol. 4 No. 9 pp. 2159–2165.

Marion M. Bradford; "A Rapid and Sensitive Method for the Quantitation of Microgram Quantities of Protein Utilizing the Principle of Protein–Dye Binding"; *Analytical Biochemistry*; Jan. 29, 1976; pp. 248–254.

Helaine Carrer, Tich Noel Hockenberry, Zora Svab, Pal Maliga; "Kanamycin resistance as selectable marker for plastid transformation in tobacco"; *Mol Gen Genet*; Apr. 6, 1993; 241: 50–56.

Helaine Carrer, Tich Noel Hockenberrry, Zora Svab, Pal Maliga; "Kanamycin resistance as selectable marker for plastid transformation in tobacco"; *Mol Gen Genet*; Apr. 6, 1993; 241: 50–56.

Francois Chaumont, Marcio De Castro Silva Filho, Didier Thomas, Serger Leterme and Marc Boutry; "Truncated presequences of mitochondrial $F_1$–ATPase $\beta$ subunit from Nicotiana plumbaginifolia transport CAT and GUS proteins into mitochondria of transgenic tobacco"; *Plant Molecular Biology*; Dec. 15, 1993; 24: pp. 631–641.

O.L. Gamborg, R.A. Miller and K. Ojima; "Nutrient Requirements of Suspension Cultures of Soybean Root Cells"; *Experimental Cell Research*; Jun. 7, 1967; 50, pp. 151–158.

Francois Guerineau, Sally Woolston, Louise Brooks and Philip Mullineaux; "An expression cassette for targeting foreign proteins into chloroplasts"; *Nucleic Acids Research*; Sep. 23, 1988; vol. 16, No. 23 p. 11380.

Q.H. Gibson; "The Direct Determination of the Velocity Constant of the Reaction $Hb_4(CO)_3+CO \rightarrow Hb_4(CO)_4$"; *Haemoglobin Kinetics*: May 2, 1956; 134, pp. 123–134.

Orit Edelbau, Dana Stein, Neta Holland, Yedidiah Gafni, Orna Livneh, Daniela Novick, Menachem Rubinstein and Ilan Sela; "Expression of Active Human Interferon–$\beta$ in Transgenic Plants"; *Journal of Interferon Research*; Aug. 19, 1992; 12, pp. 449–453.

Hanahan, D., "Techniques for Transformation of *E. coli*", *DNA Cloning* vol. 1: *A Practical Approach*, Chapter 6, pp. 109–135 (1985).

Douglas Hanahan; "Studies on Transformation of *Escherichia coli* with Plasmids"; *J. Mol. Biol.*; Oct. 11, 1982; 166, pp. 557–580.

Douglas Hanahan; "Techniques for Transformation of *E. coli*"; *DNA cloning* vol. 1, *a practical approach*; Ch. 6, pp. 109–135.

Andrew Hiatt and Julian K–C. Ma; "Monoclonal antibody engineering in plants"; *FEBS Letters*; May 11, 1992; vol. 307, No. 1, pp. 71–75.

Stephen J. Hoffman, Douglas L. Looker, Jeanne M. Roehrich, Paul E. Cozart, Steven L. Durfee, John L. Tedeso, and Gary L. Stetler; "Expression of fully functional tetrameric human hemoglobin in *Escherichia coli*"; *Proc. Natl. Acad. Sci. USA*; Nov. 1990; vol. 87, pp. 8521–8525.

R. B. Horsch, J.E. Fry, N.L. Hoffmann, D. Eichholtz, S.G. Rogers, R.T. Fraley; "A Simple and General Method for Transferring Genes into Plants"; *Science*; Mar. 8, 1985; vol. 227, pp. 1229–1231.

1995, International Hemoglobin Information Center Variant List; *Hemoglobin*; pp. 37, 39–59, 124–125.

Timm–H. Jessen, Noboru H. Komiyama, Jeremy Tame, Josee Pagnier, Daniel Shih, Ben Luisi, Giulio Fermi, and Kiyoshi Nagal; "Production of Human Hemoglobin in *Escherichia coli* Using Cleavalbe Fusion Protein Expression Vector"; *Methods in Enzymology*; 1994; vol. 231, pp. 347–365.

C.P. Joshi; "An inspection of the domain between putative TATA box and translation start site in 79 plant genes"; *Nucleic Acids Research*; Jul. 14, 1987; vol. 15, No. 16, pp. 6643–6653.

Jean Kister, Claude Poyart and Stuart J. Edelstein; "An Expanded Two–state Allosteric Model for Interactions of Human Hemoglobin A with Nonsaturating Concentrations of 2,3–Diphosphoglycerate"; *Journal of Biological Chemistry*; Dec. 3, 1986; vol. 262, No. 25, pp. 12085–12091.

Enno Krebbers, Llydia Herdies, Ann De Clercq, Jef Seurinck, Jan Leemans, Jozef Van Damme, Magdalena Segura, Godelieve Gheysen, Marc Van Montagu and Joel Vandekerckhove; "Determination of the Processing Sites of an Arabidopsis 2S Albumin and Characterization of the Complete Gene Family"; *Plant Physiology*; Apr. 5, 1988; pp. 859–866.

Michael C. Marden, Jean Kister and Claude Poyart; "Allosteric Equilibrium Measurements with Hemoglobin Valency Hybrids"; *Methods in Enzymology*; 1994; vol. 232, p. 71–86.

Hugh S. Mason, Dominic Man–Kit Lam and Charles J. Arntzen; "Expression of hepatitis B surface antigen in transgenic plants"; *Proc. Natl. Acad. Sci. USA*; Dec. 1992; vol. 89, pp. 11745–11749.

Maurice M. Moloney, Dana Parmenter, Gus Van Rooijen and Larry A. Holbrook; "Oleosins as Carriers for High–value Peptides in Plant Seeds"; *Production of Recombinant Proteins in Plants*; Jul. 1994; pp. 36–38.

Toshio Murashige and Folke Skoog; A Revised Medium for Rapid Growth and Bio Assays with Tobacco Tissue Cultures; *Physiologia Plantarium*; 1962; vol. 15, pp. 473–497.

Biyoshi Nagai and Hans Christian Thogersen; "Synthesis and Sequence–Specific Proteolysis of Hybrid Proteins Produced in *Escherichia coli*"; *Vectors for Expression of Cloned Genes*; 1987; pp. 461–481.

Kiyoshi Nagai, Max F. Perutz, and Claude Poyart; Oxygen binding properties of human mutant hemoglobins synthesized in *Escherichia coli*; *Proc. Natl. Acad. Sci. USA*: Nov. 1985; vol. 82, pp. 7252–7255.

M.F. Perutz; "Stereochemistry of Cooperative Effects in Haemoglobin"; *Nature*; Nov. 21, 1970; vol. 228, pp. 726–739.

David Russell; "Production of Industrial and Biopharmaceutical Proteins in Transgenic Plants"; *Production of Recombinant Proteins in Plants*; Jul. 24–27, 1994; p. 43.

J. Sambrook, E.F. Fritsch and T. Maniatis; Molecular Cloning: A Laboratory Manual; Second Edition.; Cold Spring Harbor Laboratory Press, Cold Spring Harbor, NY; 1989.

F. Sanger, S. Nicklen, and A.R. Coulson; "DNA sequencing with chain–terminating inhibitors"; *Proc. Natl. Acad. Sci. USA*; Dec. 1977, vol. 74, No. 12, pp. 5463–5467.

D. Stephen, C. Jones and J. Paul Schofield; A rapid method for isolating high quality plasmid DNA suitable for DNA sequencing; *Nucleic Acids Research*; Sep. 26, 1990; vol. 18, No. 24, pp. 7463–7464.

Zora Svab, Peter Hajdukiewicz, an Pal Maliga; "Stable transformation of plastids in higher plants"; *Proc. Natl. Acad. Sci. USA*; Nov. 1990; vol. 87, pp. 8526–8530.

Mark E. Swanson, Michael J. Martin, J. Kevin O'Donnell, Kathy Hoover, William Lago, Victoria Huntress, Cynthia T. Parsons, Carl A. Pinkert, Stephen Pilder and John S. Logan; "Production of Functional Human Hemoglobin in Transgenic Swine"; *Bio/Technology*; May 1992; vol. 10. pp. 557–559.

Peter C. Symons, Ben M. M. Dekker, Barbara Schrammeijer, Theo C. Verwoerd, Peter J. M. Van Den Elzen and Andre Hoekema; "Production of Correctly Processed Human Serum Albumin in Transgenic Plants"; *Bio/Technology*; Mar. 1990; vol. 8, pp. 217–221.

Joel Vanderkerckhove, Jozef Van Damme, Mieke Van Lusebettens, Johan Botterman, Marc De Block, Martine Vandewiele, Ann De Clercq, Jan Leemans, Marc Van Montagu and Enno Krebbers; "Enkephalins Produced in Transgenic Plants using Modified 2S Seed Storage Proteins"; Sep. 1989; vol. 7, pp. 929–932.

Michael Wagenbach, Katherine O'Rourke, Laura Vitez, Anna Wieczorek, Stephen Hoffman, Steven Durfee, John Tedesco and Gary Stetler; "Synthesis of Wild Type and Mutant Human Hemoglobins in Saccharamyces Cervisine"; *Bio/Technology*; Jan. 1991; vol. 9, pp. 57–61.

J.T. Wilson, L. B. Wilson, J. K. Deriel, L. Villa–Komaroff, A. Efstratiadis, B.G. Forget and S.M. Weissman; "Insertion of Synthetic copies of human globin genes into bacterial plasmids"; *Nucleic Acids Research*; Feb. 1978; vol. 5, No. 2, pp. 563–581.

Robert Kay, Amy Chan, Mark Daly and Joan McPherson; "Duplication of CaMV 35S Promoter Sequences Creates a Strong Enhancer for Plant Genes"; *Science*; Jun. 5, 1987; vol. 236, pp. 1299–1302.

A. Franck, H. Guilley, G. Jonard, K. Richards and L. Hirth; "Nucleotide Sequence of Cauliflower Mosaic Virus DNA"; *Cell*; Aug. 1980; vol. 21, pp. 285–294.

A. Depicker, S. Stachel, P. Dhaese, P. Zambryski and H. M. Goodman; "Nopaline Synthase: Transcript Mapping and DNA Sequence"; *Journal of Molecular and Applied Genetics*; 1982; vol. 1, No. 6, pp. 561–573.

David McElroy, Alan D. Blowers, Barnabas Jenes and Ray Wu: "Construction of expression vectors based on the rice actin1 (Act1) 5' region for use in monocot transformation"; *Mol Gen Genet*; 1991; vol. 231, pp. 150–160.

M. Reina, I. Ponte, P. Guillen, A. Boronat and J. Palau; "Sequence analysis of a genomic clone encoding a Zc2 protein from *Zea mays* W64 A"; *Nucleic Acids Research*; Sep. 28, 1990; vol. 18, No. 21, p. 6426.

A. Dumoulin, L. Kiger, N. Griffon, C. Vasseur, J. Kister, P. Genin, M.C. Marden, J. Pagnier and C. Poyart; "Two mutations in recombinant Hb β F41(C7)Y, K82 (EF6)D show additive effects in decreasing oxygen affinity"; *Protein Science*; Oct. 31, 1995; vol. 5, pp. 114–120.

D.F. Feng, M.S. Johnson and R.F. Doolittle; "Aligning Amino Acid Sequences: Comparison of Commonly Used Methods"; *Journal of Molecular Evolution*; 1985; vol. 21, pp. 112–125.

A. Dumoulin, V. Baudin, L. Kiger, S.J. Edelstein, M. Marden, C. Poyart, and J. Pagnier; "Chimeric Hemoglobin Subunits: Functional Properties of a Recombinant β/α Hemoglobin"; *Art, Cells, Blood Subs., and Immob. Biotech.*; 1994, vol. 22(3), pp. 733–738.

Doulas Looker, Debbie Abbott–Brown, Paul Cozart, Steven Durfee, Stephen Hoffman, Antony J. Mathews, Jeanne Miller–Roehrich, Steven Shoemaker, Stephen Trimble, Giuilio Fermi, Noboru H. Komiyama, Kiyoshi Nagia and Gary L. Stetler; "A human recombinant haemoglobin designed for use as a blood substitute"; *Nature*; Mar. 19, 1992; vol. 356, pp. 258–260.

U.K. Laemmli; "Cleavage of Structural Proteins during the Assembly of the Head of Bacteriophage T4"; *Nature*, Aug. 15, 1970; vol. 227, pp. 680–685.

Harry Towbin, Theophil Staehelin and Julian Gordon; "Electrophoretic transfer of proteins from polyacrylamide gels to nitrocellulose sheets: Procedure and some applications"; *Proc. Natl. Acad. Sci. USA* Sep. 1979; vol. 76, No. 9, pp. 4350–4354.

Koziel et al., *Plant Molecular Biology*, 32:393–405 (1996).

Swanson et al., *Bio/Technology*, 10:557–559 (1992).

Kumar, "Recombinant hemoglobins as blood substitutes: a biotechnology perspective", *Proceedings for the Society of Experimental Biotechnology and Medicine*, 208:150–158 (1995).

O'Donnell et al., "Influence of the chemical nature of side chain at B108 of hemoglobin A. on the modulation of the oxygen affinity by chloride ions", *Journal of Biochemistry*, 269:27692–27699 (1994).

* cited by examiner

Structure of heme

Alpha globin sequence:

```
1    GTG CTG TCT CCT GCC GAC AAG ACC AAC GTC AAG GCC TGG GGC    45
     Val Leu Ser Pro Ala Asp Lys Thr Asn Val Lys Ala Trp Gly

46   AAG GTT GGC GCG CAC GCT GGT GAG TAT GGT GCG CTG CTG GAG    90
     Lys Val Gly Ala His Ala Gly Glu Tyr Gly Ala Glu Leu Glu

91   AGG ATG TTC CTG TCC TTC CCC ACC ACC AAG ACC TAC TTC CCG CAC  135
     Arg Met Phe Leu Ser Phe Pro Thr Thr Lys Thr Tyr Phe Pro His

136  TTC GAC CTG AGC CAC GGC TCT GCC CAG GTT AAG GGC CAC GGC AAG  180
     Phe Asp Leu Ser His Gly Ser Ala Gln Val Lys Gly His Gly Lys

181  AAG GTG GCC GAC GCG CTG ACC AAC GCC GTG GCG CAC GTG GAC GAC  225
     Lys Val Ala Asp Ala Leu Thr Asn Ala Val Ala His Val Asp Asp

226  ATG CCC AAC GCG CTG TCC GCC CTG AGC GAC CTG CAC GCG CAC AAG  270
     Met Pro Asn Ala Leu Ser Ala Leu Ser Asp Leu His Ala His Lys

271  CTT CGG GTG GAC CCG GTC AAC TTC AAG CTC CTA AGC TTC TGC CTG  315
     Leu Arg Val Asp Pro Val Asn Phe Lys Leu Leu Ser Phe Cys Leu

316  CTG GTG ACC CTG GCC GCC CAC CTC CCC GCC GAG TTC ACC CCT GCG  360
     Leu Val Thr Leu Ala Ala His Leu Pro Ala Glu Phe Thr Pro Ala

361  GTG CAC GCC TCC CTG GAC AAG TTC CTG GCT TCT GTG AGC ACC GTG  405
     Val His Ala Ser Leu Asp Lys Phe Leu Ala Ser Val Ser Thr Val

406  CTG ACC TCC AAA TAC CGT
     Leu Thr Ser Lys Tyr Arg
```

FIGURE 2

Beta globin sequence:

```
  1  GTG CAC CTG ACT CCT GAG GAG AAG TCT GCC GTT ACT GCC CTG TGG   45
     Val His Leu Thr Pro Glu Glu Lys Ser Ala Val Thr Ala Leu Trp
 46  GGC AAG GTG AAC GTG GAT GAA GTT GGT GGT GAG GCC CTG GGC AGG   90
     Gly Lys Val Asn Val Asp Glu Val Gly Gly Glu Ala Leu Gly Arg
 91  CTG CTG GTT GTC TAC CCT TGG ACC CAG AGG TTC TTT GAG TCC TTT  135
     Leu Leu Val Val Tyr Pro Trp Thr Gln Arg Phe Phe Glu Ser Phe
136  GGG GAT CTG TCC ACT CCT GAT GCT GTT ATG GGC AAC CCT AAG GTG  180
     Gly Asp Leu Ser Thr Pro Asp Ala Val Met Gly Asn Pro Lys Val
181  AAG GCT CAT GGC AAG AAA GTG CTC GGT GCC TTT AGT GAT GGC CTG  225
     Lys Ala His Gly Lys Lys Val Leu Gly Ala Phe Ser Asp Gly Leu
226  GCT CAC CTG GAC AAC CTC AAG GGC ACC TTT GCC ACA CTG AGT GAG  270
     Ala His Leu Asp Asn Leu Lys Gly Thr Phe Ala Thr Leu Ser Glu
271  CTG CAC TGT GAC AAG CTG CAC GTG GAT CCT GAG AAC TTC AGG CTC  315
     Leu His Cys Asp Lys Leu His Val Asp Pro Glu Asn Phe Arg Leu
316  CTG GGC AAC GTG CTG GTC TGT GTG CTG GCC CAT CAC TTT GGC AAA  360
     Leu Gly Asn Val Leu Val Cys Val Leu Ala His His Phe Gly Lys
361  GAA TTC ACC CCA CCA GTG CAG GCT GCC TAT CAG AAA GTG GTG GCT  405
     Glu Phe Thr Pro Pro Val Gln Ala Ala Tyr Gln Lys Val Val Ala
406  GGT GTG GCT AAT GCC CTA GCC CAC AAG TAT CAC
     Gly Val Ala Asn Ala Leu Ala His Lys Tyr His
```

FIGURE 3

METHOD FOR PRODUCING HEMIN PROTEINS USING PLANT CELLS, RESULTING PROTEINS AND PRODUCTS CONTAINING SAME

This application is a divisional of application Ser. No. 08/983,564, filed Jun. 9, 1998, now U.S. Pat. No. 6,344,600; which is a national stage of PCT/FR96/01123, filed Jul. 17, 1996.

The invention relates to a method for producing hemin proteins using plant cells, and in particular the hemin proteins capable of reversibly binding oxygen, for example hemoglobin and its derivatives, and myoglobin. It relates, in addition, to the proteins obtained using the method. The invention also relates to the genetically transformed cells and plants capable of producing these proteins, and to the nucleic acid constructs involved in the transformation. In addition, the invention relates to products, for example pharmaceutical or cosmetic products, containing these hemin proteins.

Hemin proteins are complex molecules composed of one or more polypeptide chain(s) in association with one or more ferroporphyrin nucleus or nuclei. These nuclei are composed of four pyrrole rings, juxtaposed in a closed structure and linked by methene bridges, and containing an iron atom at the center of the molecule. Hemin proteins differ from one another in the nature and the number of the polypeptide chains and in the nature of the side chains carried by the eight $\beta$ atoms of the pyrrole rings. An example of a ferroporphyrin nucleus is iron-containing protoporphyrin IX, also known by the name "protoheme" or simply "heme" (FIG. 1).

The hemin protein family comprises numerous substances which are important from the biological point of view in animals and in plants, particularly hemoglobin, myoglobin, cytochromes, peroxidases and catalases.

Hemoglobin is the main constituent of the red blood cells. Its essential function is to bind, transport and deliver the quantity of oxygen necessary for normal tissue function.

The hemoglobin molecule is composed of two types of globin chains or subunits, called $\alpha$ and $\beta$ (of 141 and 146 amino acids respectively), and linked in pairs to form a $\alpha_2\beta_2$ tetramer. Each of these subunits contains, solidly attached in a hydrophobic sac, a heme molecule (that is to say protoporphyrin IX) containing, at the center, a divalent iron atom ($Fe^{2+}$) to which a molecule of oxygen reversibly binds. Each tetrameric hemoglobin molecule therefore contains 4 iron atoms and 4 oxygen molecules which it binds during its passage through the lungs. The molecular mass of the tetramer is 64,650 D. In man, the $\alpha$ and $\beta$ chains are synthesized from two types of genes situated on chromosomes 16 and 11 respectively.

The term beta, or "nonalpha", type chains covers not only the beta chains, but also the chains called epsilon, gamma or delta.

Normally, in adults, more than 95% of the hemoglobin consists of $alpha_2$ $beta_2$ tetramer, that is to say the association of two heterologous alpha-beta dimers, associated with the catalytic complex, heme. 2% to 3% of a hemoglobin consisting of $alpha_2$ $delta_2$ tetramers, and traces of fetal hemoglobin $alpha_2$ $gamma_2$ exist.

The tetrameric human hemoglobin molecule exists in two quaternary forms or structures depending on whether oxygen is bound or not to the iron atoms. In the presence of oxygen, hemoglobin is said to be in an R (for relaxed) state and its affinity for oxygen is high. In the absence of oxygen, hemoglobin is said to be in a T (for tense) state and its affinity for oxygen is 100 times lower (Perutz, 1970). The resultant affinity is linked to the equilibrium between the concentrations of R and T forms. The higher the concentration of hemoglobin in the T form at any level of oxygenation, the lower this affinity. The affinity of hemoglobin for oxygen is regulated by the cofactor—2,3-diphosphoglycerate (DPG), a small molecule derived from the metabolism of glucose and which binds to the $\beta$ chains of tetrameric hemoglobin, reducing its affinity for oxygen.

The increase in the risks of infection by products derived from human blood (hepatitis, HIV) makes the development of an artificial oxygen carrier as substitute for blood transfusion necessary.

Techniques using recombinant DNAs have been proposed for producing the protein chains of globin.

The aim of the first techniques developed was essentially to cause the alpha and beta chains to be synthesized in *E. coli* separately (Nagaï and Thogen-Sen, 1987), involving cumbersome methods for separate expression of each of the chains. These methods could hardly be exploited on an industrial scale.

More recently, the expression of soluble and functional recombinant hemoglobin has been developed in *E. coli* (Hoffman et al., 1990, P.N.A.S., 87, 8521–8525) and *Saccharomyces cerevisiae* (Wagenbach et al., 1991, Biotechnology, 9, 57–61). Each of these systems has advantages and disadvantages. Indeed, the highest expression levels are obtained in *E. coli* which has, nevertheless, the disadvantage of producing endotoxins and of not cleaving the $NH_2$ terminal methionines contrary to *Saccharomyces cerevisiae*. In the yeast, the yields of synthesis of hemoglobin are low (3 to 5%), compared with the 10–15% obtained in *E. coli*. This currently limits the use of yeast in the context of an industrial development plan.

The use of animal cells in culture or of transgenic animals as hosts for production has also been achieved (Swanson et al., Bio/Technology, May 1992, 10, page 55). It appears that these techniques cannot currently be exploited because of low expression levels and the risks of contaminations by viruses and by prions.

The technical problem which the present invention purposes to solve is to produce hemin proteins, and in particular hemoglobin and its derivatives, in a large quantity at low costs, without the risk of viral or subviral contaminations. The inventors have provided a solution to this problem by using plant cells as host for the transformation and the production.

Various teams have already taken an interest in the production of mammalian recombinant proteins in plant cells or in transgenic plants. For example, the specific expression, in rapeseed, of leu-enkephalin has been obtained with expression levels of about 0.1% (Vanderkerckhove et al., Biotechnology, 1989, 7, 929–932).

In 1990, Sijmons et al., (Biotechnology, 1990, 8, 217–221) transferred the gene for human serum albumin into tobacco and potato cells. Regardless of the origin of the signal peptides (human or plant), human serum albumin levels of the order of 0.02% of the total proteins were obtained in the potato leaves, stems and tubers.

Other mammalian recombinant proteins have also been produced in plants: hepatitis B surface antigen (Mason et al., P.N.A.S., 1992, 89, 11745–11749); human interferon (Edelbaum J. of Interferon Res., 1992, 12, 449–453); a mouse antibody to *Streptococcus mutans,* an agent for dental caries (Hiatt and Ma, FEBS, 1992, 307, 71–75); an anti-Herpes antibody (Russel, 1994) and hirudin (Moloney, 1994).

All these research studies show that the production of mammalian recombinant proteins in plant cells is possible and that the mechanisms of protein synthesis from the DNA sequences are similar in animal cells and plant cells.

On the other hand, little information is available on the subject of the iron-containing porphyrins in plants, particularly on their structures, their synthesis pathways and the assembly of the porphyrin nuclei and the protein chains to form the hemin proteins. The production of recombinant molecules having the capacity to reversibly bind oxygen, and requiring the assembly, in the cell, of heterologous proteins and of endogenous plant porphyrins has never been described.

The invention relates to a method for producing recombinant hemin proteins using plant cells. According to the method of the invention, the plant cell is genetically modified so as to be able to express the protein component of a hemin protein. The porphyrin nucleus is produced by the cell endogenously, the assembling of the protein and porphyrin components taking place spontaneously by virtue of their high affinity for each other.

More particularly, the invention relates to a method for producing hemin proteins comprising the following steps:
i) introducing, into plant cells, one or more nucleic acid molecule(s) each of which comprises at least one sequence encoding a protein component of a hemin protein of animal origin or a variant or a portion of this protein component, and optionally a sequence encoding a selection agent;
ii) selecting the cells which have integrated the nucleic acid encoding the protein component;
iii) propagating the transformed cells, either in culture or by regenerating whole transgenic or chimeric plants;
iv) recovering, and optionally purifying, a hemin protein comprising a complex of the protein or proteins encoded by the abovementioned nucleic acid with at least one iron-containing porphyrin nucleus, or a plurality of these complexes.

The invention preferably relates to a method for producing hemin proteins comprising the following steps:
i) introducing, into plant cells, one or more nucleic acid molecule(s) each of which comprises at least one sequence encoding a protein component of a hemin protein of animal origin preferably capable of reversibly binding oxygen or a variant or a portion of this protein component, and optionally a sequence encoding a selection agent;
ii) selecting the cells which contain the nucleic acid encoding the protein component of the hemin protein;
iii) optionally, propagating the transformed cells, either in culture or by regenerating whole transgenic or chimeric plants;
iv) recovering, and optionally purifying, a hemin protein comprising a complex consisting of the protein or proteins encoded by the abovementioned nucleic acid and at least one iron-containing porphyrin nucleus, or a plurality of these complexes.

In the context of the present invention, the term "hemin protein" means any protein having an iron-containing porphyrin nucleus as prosthetic group, and in particular protoporphyrin IX as exists in human myoglobin and hemoglobin (FIG. 1). The porphyrin nucleus may also be derivatives of heme from those of human heme. The side chains are preferably hydrophobic.

The hemin proteins of the invention include in particular the hemin proteins having, as main function, the reversible binding of oxygen, that is to say myoglobin and hemoglobin, as well as the cytochromes whose role is to transport electrons. The derivatives of these proteins conserving these functions are also included in the invention.

According to a preferred variant, the hemin protein of the invention is hemoglobin or a hemoglobin-type protein. In the context of this invention, the term "hemoglobin-type protein" includes all the hemin proteins having at the same time:
i) one or more α- and/or β-globin chain(s) or variants of these polypeptides, and
ii) one or more molecules of iron-containing protoporphyrin IX, or of protoporphyrins differing from protoporphyrin IX in the nature of the side chains,
iii) having a capacity to reversibly bind oxygen, preferably with an affinity of between 10 and 50 mm Hg at 37° C., pH 7.4. More particularly, the affinity is between 20 and 30 mm Hg, by way of example, the $P_{50}$ of total blood at pH 7.2 is of 26±2 mm Hg.

In the text which follows, the term "hemoglobin-type molecule" will be used synonymously with the term "hemoglobin derivative".

In this context, a "variant" of a protein component, and particularly of α- or β-globin, means an amino acid sequence which distinguishes itself in relation to the natural sequence by one or more amino acid substitution(s), deletion (s) or insertion(s). In general, the variant exhibits at least 90%, and preferably at least 95%, homology or identity with the natural sequence. In the context of the present invention, the percentage homology between two amino acid sequences is calculated as being the number of identical amino acids plus the number of similar amino acids in the alignment of the two sequences, divided by the length of the sequences between two given positions. If, between the two given positions, the two sequences do not have the same length, the percentage homology is the number of identical and similar amino acids, divided by the length of the longest sequence. The amino acids considered to be "similar" are known in the art, see for example R. F. Feng, M. S. Jobson and R. F. Doolittle; J. Mol. Evol.; 1985; 21; 112–115. They are normally considered to be those which, within a permutation matrix, have a positive coefficient of substitution.

The term "variant" also includes fragments of polypeptide chains, for example of α- or β-globin, normally having a length of at least 90% of the parent molecule. The variants can also be made longer than the parent molecule by adding nonfunctional sequences. Preferably, the variants conserve the biological and immunological properties of the parent molecule.

The first stage of the method of the invention consists in introducing, into plant cells, one or more nucleic acid molecule(s) comprising at least one sequence encoding a protein component of a mammalian hemin protein, or a variant of this component.

When the hemin protein is a single-chain protein, for example myoglobin or cytochrome, the nucleic acid introduced into the plant cells normally comprises a copy of the sequence encoding this protein.

On the other hand, when it is an oligomeric or a multimeric protein, such as hemoglobin or hemoglobin-type molecules, the sequences encoding the various protein units are introduced into the plant cell, either within the same nucleic acid molecule, or within separate nucleic acid molecules. Preferably, for the production of hemoglobin and its derivatives, the sequences encoding α- and β-globin, or their variants, are within the same vector, called co-expression vector. The vector may comprise one or more copy(ies) of each encoding sequence.

Alternatively, the sequences encoding α- and β-globin, or their variants, may be present on separate nucleic acid molecules. According to this variant, the two molecules may be introduced into the same plant cell, provided that an appropriate selection system is available. Another technique consists in introducing one of the molecules into a first plant cell, and the other into a second plant cell. Each of the transformed cells is then regenerated into a whole plant, it then being possible for the plants thus obtained to be crossed in order to give a progeny capable of producing both the α and β chains. This approach can be used to optimize the yield of hemoglobin.

The nucleic acid molecules introduced into the plant cell during the first stage of the method are also part of the invention. Generally, these nucleic acids comprise:
i) one or more sequence(s) encoding a protein component of an animal hemin protein, and
ii) one or more sequence(s) encoding a targeting signal of plant origin, and/or sequences for regulation of transcription which are recognized by a plant cell.

More particularly, the nucleic acid of the invention comprises:
i) one or more sequence(s) encoding a protein component of an animal hemin protein, the said protein having the capacity to reversibly bind oxygen, and
ii) sequences for regulation of transcription which are recognized by a plant cell, comprising a promoter and sequences for regulation of termination, and
iii) one or more sequence(s) encoding a targeting signal of plant origin.

Preferably, the sequences encoding the protein component encode animal α- or β-globin, for example of human or bovine origin, or the variants thereof. In this manner, the properties of the molecule, and in particular the affinity for oxygen and the stability, can be optimized.

Among these modifications, it is possible, for example, to introduce into one or into both of the α- and β-globin chains, by site-directed mutagenesis, one or two sequence difference(s) in order to reduce the affinity for oxygen. These mutations may be chosen from examples of natural mutations (see Table I), or from the mutations indicated by examination of the three-dimensional model of natural hemoglobin A.

TABLE I

Some mutated human hemoglobins
(Int. Hemoglobin Center, 1995)

| Abnormal hemoglobin | Normal residues and positions | Replacement |
|---|---|---|
| | α chain (SEQ ID NO: 31) | |
| I | 16 Lys | Glu |
| $G_{Honolulu}$ | 30 Glu | Gln |
| Norfolk | 57 Gly | Asp |
| $M_{Boston}$ | 58 His | Tyr |
| $G_{Philadelphia}$ | 68 Asn | Lys |
| $O_{Indonesia}$ | 116 Glu | Lys |
| | β chain (SEQ ID NO: 33) | |
| C | 6 Glu | Lys |
| S | 6 Glu | Val |
| $G_{San\ José}$ | 7 Glu | Gly |
| E | 26 Glu | Lys |
| $M_{Saskatoon}$ | 63 His | Tyr |
| Zurich | 63 His | Arg |
| $M_{Milwaukee}$ | 67 Val | Glu |

TABLE I-continued

Some mutated human hemoglobins
(Int. Hemoglobin Center, 1995)

| Abnormal hemoglobin | Normal residues and positions | Replacement |
|---|---|---|
| $D_{Punjab}$ | 121 Glu | Gln |
| Mequon | 41 Phe | Tyr |
| Providence | 82 Lys | Asp |

In a very advantageous manner, the mutants whose functional properties correspond to the physiological conditions for oxygen transport will be used: reversible binding, cooperativity and low speed of autooxidation. Among the mutants, there will be preferably used the double mutants $α_2β_2$F41Y,K82D (that is to say a mutant whose β chain comprises the following modifications: Phe-41 is replaced by Tyr, and Lys-82 is replaced by Asp) or $α_2β_2$F41Y,K66T (that is to say a mutant whose β chain comprises the following modifications: Phe-41 is replaced by Tyr, and Lys-66 is replaced by Thr) which correspond to these functional characteristics.

The modifications of the α and β chains may also be carried out in order to stabilize the molecule, that is to say to avoid the dissociation of the tetramer into small-sized dimers which are rapidly filtered by the kidneys and which limit the intravascular life of hemoglobin. Covalent bridging, with the aid of phosphate or diaspirin, has been demonstrated as being an effective technique for stabilizing the tetramer (Benesch and Kwong, 1994). The same result can be obtained through modifications of the amino acid chain. The α subunits are produced in an alpha-alpha dimeric form linked by a glycyl residue. In this form, they conserve their capacity to correctly assemble onto the beta partner subunits and onto heme in order to form a soluble hemoglobin. This hemoglobin can no longer dissociate into dimers because the tetrameric structure is stabilized by a covalent bond (peptide bond) between the alpha-beta dimers. This technique makes it possible to increase the intravascular half-life of the molecule.

Among the variants, it is also possible to use a hybrid protein composed of a portion of the alpha chain and a portion of the beta chain.

According to a preferred variant of the invention, the nucleic acid comprises, in addition to the sequences encoding α- or β-globin, sequences encoding targeting signals. Preferably, these signals are chloroplast or mitochondrial targeting signals. The expression and/or accumulation of the recombinant proteins in these organelles is particularly preferred because of the availability of endogenous iron-containing porphyrins which are found here. The yield of hemin proteins is therefore increased. In addition, the targeting of the proteins toward the chloroplasts and the mitochondria avoids glycosylation of the protein, which may be advantageous since the natural hemoglobin molecule is not glycosylated.

As an example of chloroplast targeting signals, there may be mentioned the sequence encoding the transit peptide of the precursor of the small subunit of ribulose 1,5-diphosphate carboxylase of *Pisum sativum* (see examples). As mitochondrial targeting signals, there may be mentioned the sequence encoding the transit peptide of the precursor of the beta subunit of mitochondrial ATP-aseF1 of *Nicotiana plumbaginifolia* (see examples).

These transit peptides, as well as the N-terminal methionine, are normally cleaved in the chloroplasts or the mitochondria. The expression of the proteins in the plastids therefore also has the advantage of producing a molecule lacking N-terminal methionine as natural molecule.

According to another variant, the targeting sequences may be sequences encoding an N-terminal signal peptide ("prepeptide"), optionally in association with a signal responsible for retaining the protein in the endoplasmic reticulum (KDEL-type signal), or a vacuolar targeting signal or "propeptide". The presence of the N-terminal signal peptide or prepeptide allows the penetration of the nascent protein into the endoplasmic reticulum where a certain amount of post-translational processing occurs, particularly the cleaving of the signal peptide, the N-glycosylations, if the protein in question has N-glycosylation sites, and the formation of disulfide bridges. Among these various signals, the prepeptide responsible for the targeting of the protein into the endoplasmic reticulum, is dominant. It is normally a hydrophobic N-terminal signal peptide having between 10 and 40 amino acids and being of animal or plant origin. Preferably, it is a prepeptide of plant origin, for example that of sporamine, barley lectin, plant extensin, α-mating factor, pathogenesis protein 1 or 2.

Normally, the signal peptide is cleaved by a peptidase signal upon the co-translational introduction of the nascent polypeptide into the lumen of the RER. The mature protein no longer contains this N-terminal extension.

The targeting sequences can, besides the prepeptide, also comprise an endoplasmic retention signal, consisting of the KDEL, SEKDEL or HEKDEL peptides. These signals normally exist at the C-terminal end of the protein and remain on the mature protein. The presence of this signal tends to increase the recombinant protein yields.

The targeting signals may, besides the prepeptide, also comprise a vacuolar targeting signal or "propeptide". In the presence of such a signal, after passing into the RER, the protein is targeted toward the vacuoles of the aqueous tissues, the leaves for example, as well as to the protein bodies of the storage tissues, for example the seeds, tubers and roots. The targeting of the protein toward the protein bodies of the seed is particularly advantageous because of the capacity of the seed to accumulate proteins, up to 40% of the proteins relative to the dry matter, in cellular organelles derived from the vacuoles, called protein bodies and because of the possibility of stocking, for several years, the seeds containing the recombinant proteins in the dehydrated state.

As propeptide, it is possible to use a signal of animal or plant origin, the plant signals being particularly preferred, for example prosporamine. The propeptide may be N-terminal ("N-terminal targeting peptide" or NTTP), or C terminal (CTTP) Since the propeptides are normally cleaved upon entry of the protein into the vacuole, it is not present in the mature protein.

The use of the signal peptide or prepeptide can lead to the glycosylation of the protein. Normally, globin has no N-glycosylation sites, but these may be introduced by mutagenesis. The α and β chains can also have O-glycosylation sites.

In the absence of any targeting signal, the protein is expressed in the cytoplasm.

The nucleic acid introduced into the plant cell may also comprise sequences for regulation of transcription which are recognized by the plant cell. The nucleic acid is in this case a "chimeric gene". The regulatory sequences comprise one or more promoter(s) of plant or viral origin or obtained from *Agrobacterium tumefaciens*. They may be constitutive promoters, for example the CaMV 35S, the double 35S, the Nos or OCS promoters, or promoters specific for certain tissues such as the grain or specific for certain phases of development of the plant. As promoters specific for seeds, there may be mentioned the promoter of the gene for napin and for the acyl carrier protein (ACP) (EP-A-0,255,378), as well as the promoters of the AT2S genes of *Arabidopsis thaliana*, that is to say the PAT2S 1, PAT2S2, PAT2S3 and PAT2S4 promoters (Krebbers et al., Plant Physiol., 1988, vol. 87, pages 859–866). It is particularly preferable to use the cruciferin or phaseolin promoter or pGEA1 and pGEA6 of *Arabidopsis*, promoters of genes of the "em, Early Methionine labeled protein" type, which is strongly expressed during the phases of drying of the seed.

It is possible to envisage using "enhancers" to improve the efficiency of expression. When the transformation occurs directly in the chloroplast and mitochondrial genomes, gene promoters specific for these compartments can be used.

The sequences for regulation of transcription normally comprise sequences for termination of transcription which are of plant or of viral origin, for example 35S, or of bacterial origin (*Agrobacterium*).

When the transforming nucleic acid does not comprise regulatory sequences, it is preferable to add onto each end of the nucleic acid a DNA sequence homologous to the genomic sequences which are adjacent to a specific insertion site in the genome. This allows the integration of the construct by homologous recombination, at a site where endogenous regulatory sequences can control the expression of the heterologous sequences.

The nucleic acids of the invention may also comprise one or more intron(s), preferably of plant origin. These introns, which are obtained from a plant gene, are introduced artificially so as to increase the efficiency of expression of the heterologous sequence.

Indeed, it has been demonstrated, particularly in monocotyledonous plants, that the insertion of an intron into the untranslated 5' portion of a gene, that is to say between the site of initiation of transcription and the site of initiation of translation, leads to an improvement in the stability of the messenger, and consequently, to a better expression. The intron(s) used in this manner are obtained preferably from a monocotyledonous plant such as maize. This is preferably, but not necessarily, the first intron of the gene.

The nucleic acid sequence encoding α- and β-globin and its variants is normally cDNA. Appropriate sequences are illustrated in FIGS. 2 and 3 (SEQ ID NO: 30 and SEQ ID NO: 32, respectively), and degenerate sequence can also be used as well as the sequences of the variants as defined above.

The introduction of a nucleic acid molecule(s) into the plant cell can be carried out in a stable manner either by transformation of the nuclear genome, or by transformation of the chloroplast genome of the plant cell, or by transformation of the mitochondrial genome.

For the transformation of the nuclear genome, conventional techniques may be used. All known means for introducing foreign DNA into plant cells may be used, for example *Agrobacterium*, electroporation, protoplast fusion, particle gun bombardment, or penetration of DNA into cells such as pollen, microspore, seed and immature embryo. Viral vectors such as the Gemini viruses or the satellite viruses may also be used as introducing means. *Agrobacterium tumefaciens* and *rhizogenes* constitute the preferred means. In this case, the sequence of the invention is introduced into an appropriate vector with all the necessary regulatory sequences such as promoters, terminators and the like, as well as any sequence necessary for selecting the transformants which have integrated the heterologous sequences.

The transformation of the nuclear genome of the plant cell is often carried out using the targeting signals mentioned above and which determine the cellular compartment where the expression and/or accumulation of the protein will occur.

According to another variant of the invention, the introduction of the nucleic acid into the plant cell can be carried out by the transformation of the mitochondrial or chloroplast genomes (see for example Carrer et al., Mol. Gen. Genet., 1993, 241, 49–56).

Techniques for direct transformation of the chloroplasts or the mitochondria are known per se and may comprise the following steps:
i) introducing transformant DNA by the biolistic technique (Svab et al., P.N.A.S., 1990, 87, 8526–8530);
ii) integrating the transformant DNA by two homologous recombination events;
iii) selectively removing copies of the wild-type genome during repeated cell divisions on selective medium.

In order to allow the homologous recombination of the transformant DNA, two DNA fragments homologous to the genomic sequences, for example the rbcL and ORF 512 genes are added to each end of the DNA to be inserted into the genome.

The direct transformation of the chloroplasts or mitochondria has the advantage of substantially increasing the yield of hemoglobin but the N-terminal methionine is retained.

According to another variant of the invention, the heterologous nucleic acid can be introduced into the plant cell by means of a viral vector.

The method of the invention comprises a step of detecting the hemin proteins and in particular hemoglobin and its derivatives. This makes it possible to verify if the plant or the plant cell is capable, not only of expressing the heterologous proteins, but also of assembling them correctly with the porphyrin nucleus. For the hemoglobin in a complex environment containing other chromophores or molecules which scatter light, detection by time-resolved optical spectroscopy will be advantageously used. This technique is described in detail in the examples. Other detection techniques consist in using antibodies specific for the alpha or beta globin chains or their variants. The spectrometric and immunological techniques can be used in association with each other. The use of these techniques makes it possible to select the plants which are capable of producing hemoglobin and its derivatives according to the invention.

The method of the invention comprises, in addition, a step of recovering or extracting hemoglobin or its derivatives from plant tissues. The extraction is normally carried out by grinding the tissues, for example leaves or grains, in an appropriate buffer, filtering the ground product, precipitating the proteins in the supernatant, centrifuging and taking up the pellet in an appropriate buffer with dialysis. A partial purification step can also be carried out at this stage by chromatography on an anion-exchange column.

The tetramer of hemoglobin, or of its derivatives, is purified by two successive chromatographies on an ion-exchange resin followed by a step of concentrating and saturating the concentrate with carbon monoxide. These techniques are described in detail in the examples.

When the expression of hemoglobin and of its derivatives take place under the control of a constitutive promoter, such as the 35S double promoter, an expression level of at least 1% hemoglobin compared with the total proteins may be obtained. The proteins represent about 10% of the dry mass of the leaf and a ton of dry tobacco leaves is harvested per hectare. It is therefore possible to obtain of the order of 100 grams of hemoglobin per hectare of tobacco cultivated, assuming that only 10% of the hemoglobin produced is purified.

The method of the invention therefore allows the production of hemoglobin at very low costs with a higher production capacity than that obtained using fermenters of the culture of bacteria or yeast.

Besides the method of transformation, the invention also includes vectors comprising one or more nucleic acid(s) or chimeric gene(s) defined above. As an example of vectors, there may be mentioned binary vectors or plasmids, viral vectors such as gemini viruses or the CaMVs.

The invention also relates to the plant cells transformed with the nucleic acid sequences of the invention. Preferably, they are transformed plant cells capable of producing one or more hemoglobin(s) or derivatives of hemoglobin according to the invention.

They may be plant cell cultures in vitro, for example in liquid medium. Various modes of culture ("batch", "fed batch" or continuous) for this type of cells are currently under study. The "batch" cultures are comparable to those carried out in an Erlenmeyer flask since the medium is not changed, these cells thus have only a limited quantity of nutrient materials. The "fed batch" culture corresponds, for its part, to a "batch" culture with programmed supply of substrate. For a continuous culture, the cells are supplied continuously with nutrient medium. An equal volume of the biomass-medium mixture is removed in order to maintain the volume of the reactor constant. The quantities of plant biomass which can be envisaged with cultures in bioreactors are variable depending on the plant species, the mode of culture and the type of bioreactor. Under certain conditions, biomass densities of about 10 to 30 g of dry weight per liter of culture can be obtained for species such as *Nicotiana tabacum*, *Vinca rosea* and *Catharanthus roseus*.

The cells of the invention can also be immobilized, which makes it possible to obtain a constant and prolonged production of hemoglobin. The separation of the hemoglobin and the plant biomass is also facilitated. As immobilization method, there may be mentioned immobilization in alginate or agar beads, inside polyurethane foam, or alternatively inside hollow fibers.

The cells of the invention may also be root cultures. The roots cultivated in vitro, in a liquid medium, are called "Hairy roots", they are roots transformed by the bacterium *Agrobacterium rhizogenes*.

Instead of producing the hemoglobin of the invention by culturing plant cells, it is possible to regenerate chimeric or transgenic plants from transformed explants, using techniques known per se.

As appropriate plants, there may be mentioned the Angiospermae comprising monocotyledonous and dicotyledonous plants. More particularly, there may be mentioned tobacco, species belonging to botanic families such as leguminous plants (for example beans, peas and the like), cruciferous plants (for example cabbage, raddish, rapeseed and the like), Solanaceae (for example tomatoes, potato and the like), Cucurbitaceae (for example melon), Chenopodiaceae (for example beetroot), Umbelliferae (for example carrots, celery and the like). There may also be mentioned cereals such as wheat, maize, barley, triticale and rice, oleaginous plants such as sunflower and soybean. Tobacco, potato, tomato and maize are particularly preferred. For potato, the expression takes place preferably in the tubers.

The invention also relates to the seeds of transgenic plants capable of producing hemoglobin as well as their progeny.

The invention also relates to the hemin proteins which may be obtained by the method of the invention, in particular, the hemin proteins capable of reversibly binding oxygen, for example the hemoglobins and derivatives thereof.

The hemoglobins of the invention are capable of binding $O_2$ in a reversible manner with an affinity ($P_{50}$) preferably close to physiological values (37° C.), pH 7.40). The affinity of the molecule for $O_2$ is expressed as $P_{50}$: that is to say the partial pressure of $O_2$ when hemoglobin or its derivatives is 50% saturated. The $P_{50}$ is measured according to the usual techniques, for example by means of an analyzer which measures the percentage $O_2$ saturation as a function of the $O_2$ pressure (Kister et al., 1987). Normally, the hemoglobins of the invention have an acceptable autooxidation rate in order to minimize the formation of methemoglobin which is unsuited to the transport of $O_2$. This characteristic can be measured by the absorption spectrum.

Preferably, the hemoglobins of the invention are tetramers, preferably alpha$_2$ beta$_2$, beta$_4$, or optionally tetramers of chimeric α/β subunits (Dumoulin et al., 1994, Art. Cells, Blood Subst., and Immob. Biotech., 22, 733–738) or multiples of four subunits. The physical size of the complex should be at least that of the tetramer in order to avoid its filtration by the kidneys.

The hemin proteins of the invention can be used in numerous pharmaceutical, cosmetic or industrial applications. The invention relates in particular to pharmaceutical compositions comprising one or more hemin protein(s) according to any one of Claims 43 to 52, in association with a physiologically acceptable excipient.

In the pharmaceutical field, all the conditions requiring an improvement of the transport of oxygen can be treated with the hemoglobins of the invention, these conditions comprising the following:

acute or chronic hemorrhage, states of shock, coronary or sylvian angioplasties, treatments of solid tumors, sensitization to gammatherapy, preservation of organs before transplant and during transport, malignant hemopathies.

The hemoglobins of the invention are normally used in the form of an injection in solutions optionally stabilized as regards the tetrameric form of the complex (for example addition of pyridoxal phosphate or diaspirin) as regards autooxidation. It is also possible to use suspensions of hemoglobin grafted on a support in order to increase the lifetime in the bloodstream. The support may be any conventional support in this domain, for example polysaccharides.

Various aspects of the invention are illustrated in the figures:

FIG. 1: Iron-containing protoporphyrin III (IX),

FIG. 2: cDNA sequence of human α-globin (423 base pairs; SEQ ID NO: 30), and corresponding protein, (SEQ ID NO: 31), FIG. 3: cDNA sequence of human β-globin (438 base pairs; SEQ ID NO: 32), and corresponding protein, (SEQ ID NO: 33)

Figure 4:
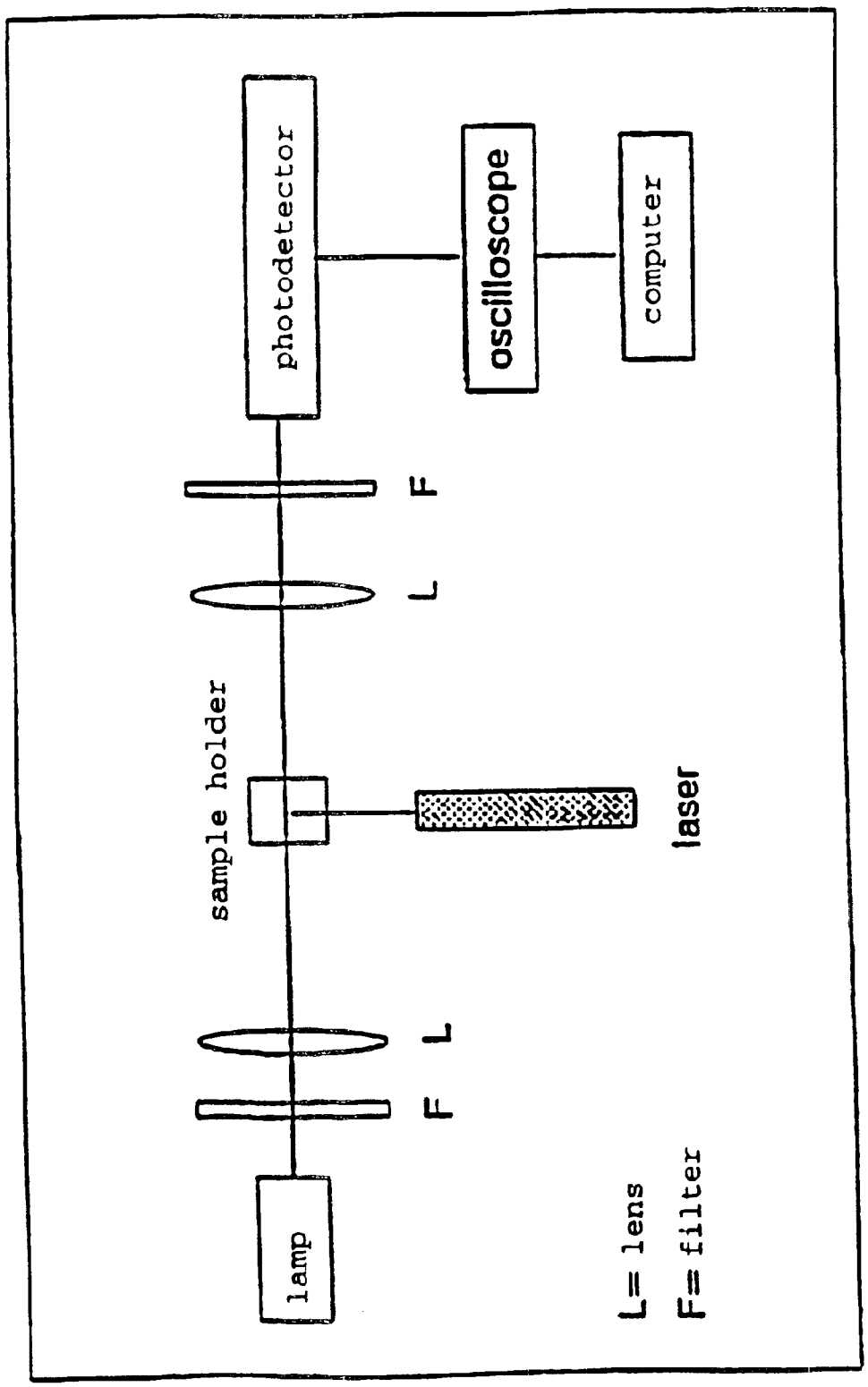

FIG. 4: Experimental device for flash photolysis. A pulsed laser serves for the photodissociation of the Hb ligands: (HbCO→Hb+CO). A second optical beam, oriented at 90°, detects changes in absorption as a function of time after dissociation.

Figure 5:
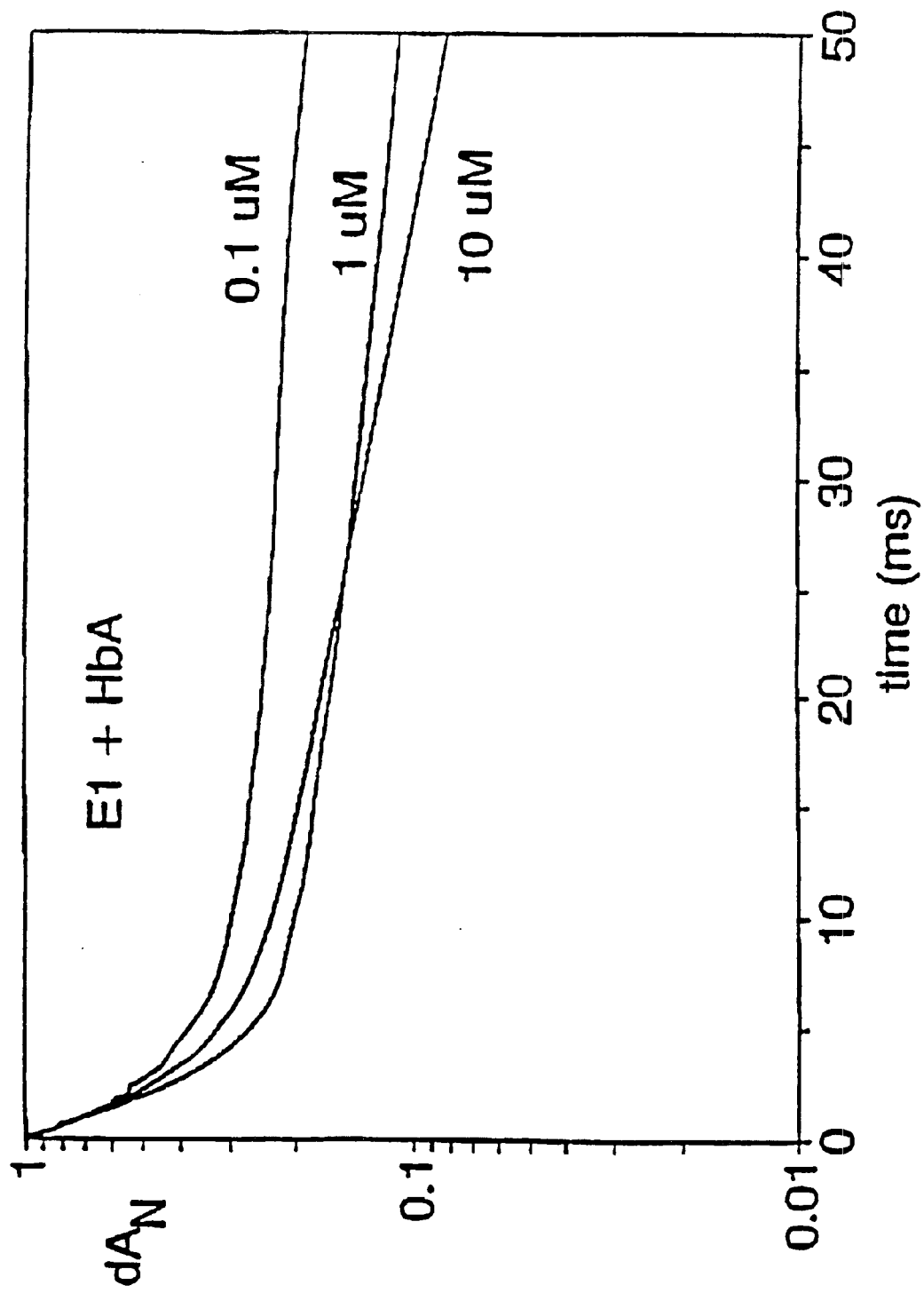

FIG. 5: Kinetics of bimolecular recombination of CO with hemoglobin in plant extract. The two phases correspond to the two allosteric states of Hb: R (rapid) and T (slow). Conditions: 0.1 atm CO, pH 6-6, 25° C., about 50% dissociation, 0–1, 1 and 10 μM Hb.

Figure 6:
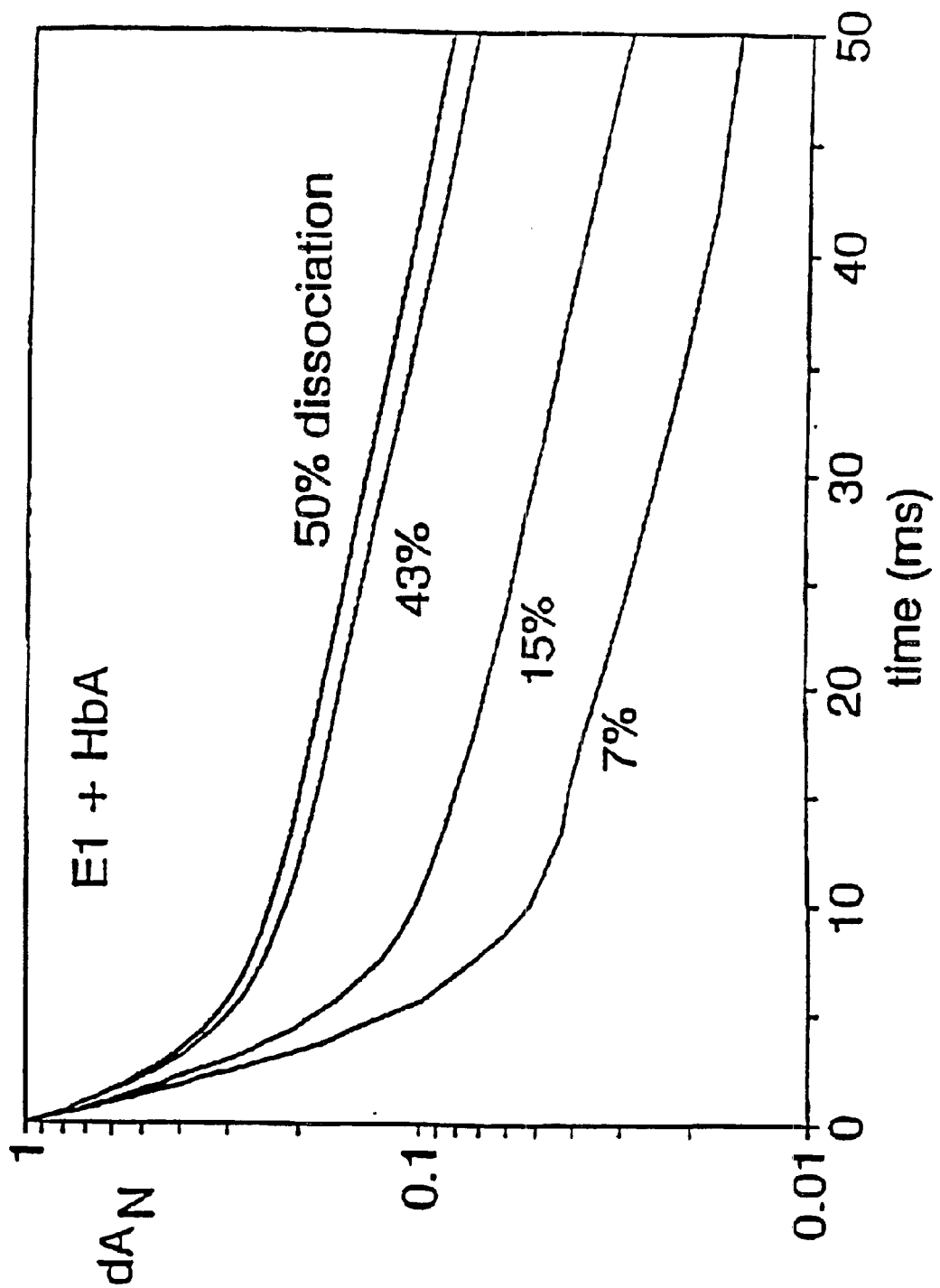

FIG. 6: Kinetics of recombination of CO with hemoglobin as a function of the percentage dissociation (by variation of the laser energy). The kinetics are sensitive to the number of ligands dissociated (1 to 4). At a high level of dissociation, Hb (deoxy or mono-ligand containing) shifts toward the slow form "T". At a low laser energy, the tetramers (mainly with three ligands) remain in the rapid form "R".

Figure 7:
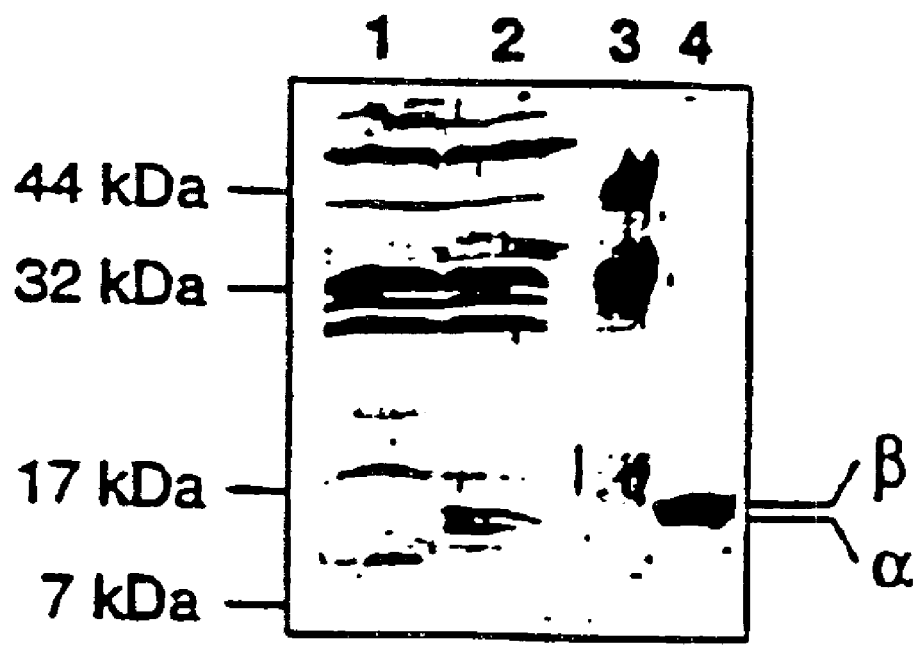

FIG. 7: Western-blot analysis of the extract of the seeds of the transgenic tobacco T26-22 transformed with the plasmid pBIOC59. The extracts of seeds (75 μg of proteins) of a nontransformed tobacco (1) and of a transgenic tobacco (T26-22) (2), molecular weight markers (3) and HbA (50 ng) (4) are separated by SDS-PAGE 17% electrophoresis under reducing conditions. The Western blotting is carried out under the conditions described in section X.a. The molecular weight markers and the α and β globins are indicated.

Figure 8:
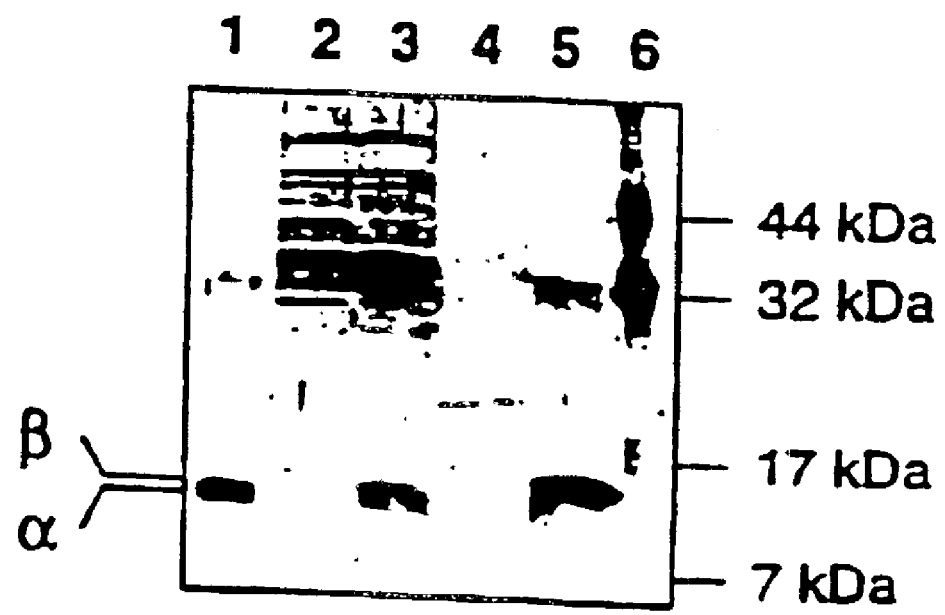

FIG. 8: Western-blot analysis of the fractions obtained during partial purification. The proteins in the fractions eluted from Sephacryl S-100 (37 μg), from S-Sepharose (30 μg) which are obtained during purification from mixtures of control seeds [(2) and FE-Control (4) respectively] and of seeds accumulating rHb [(3) and FE-rHb (5) respectively], HbA (50 ng) (1) and molecular weight markers (6) were separated by SDS-PAGE 17% electrophoresis under reducing conditions. The Western blotting is carried out under the conditions described in section X.a. The molecular weight markers and the α and β globins are indicated.

Figure 9:
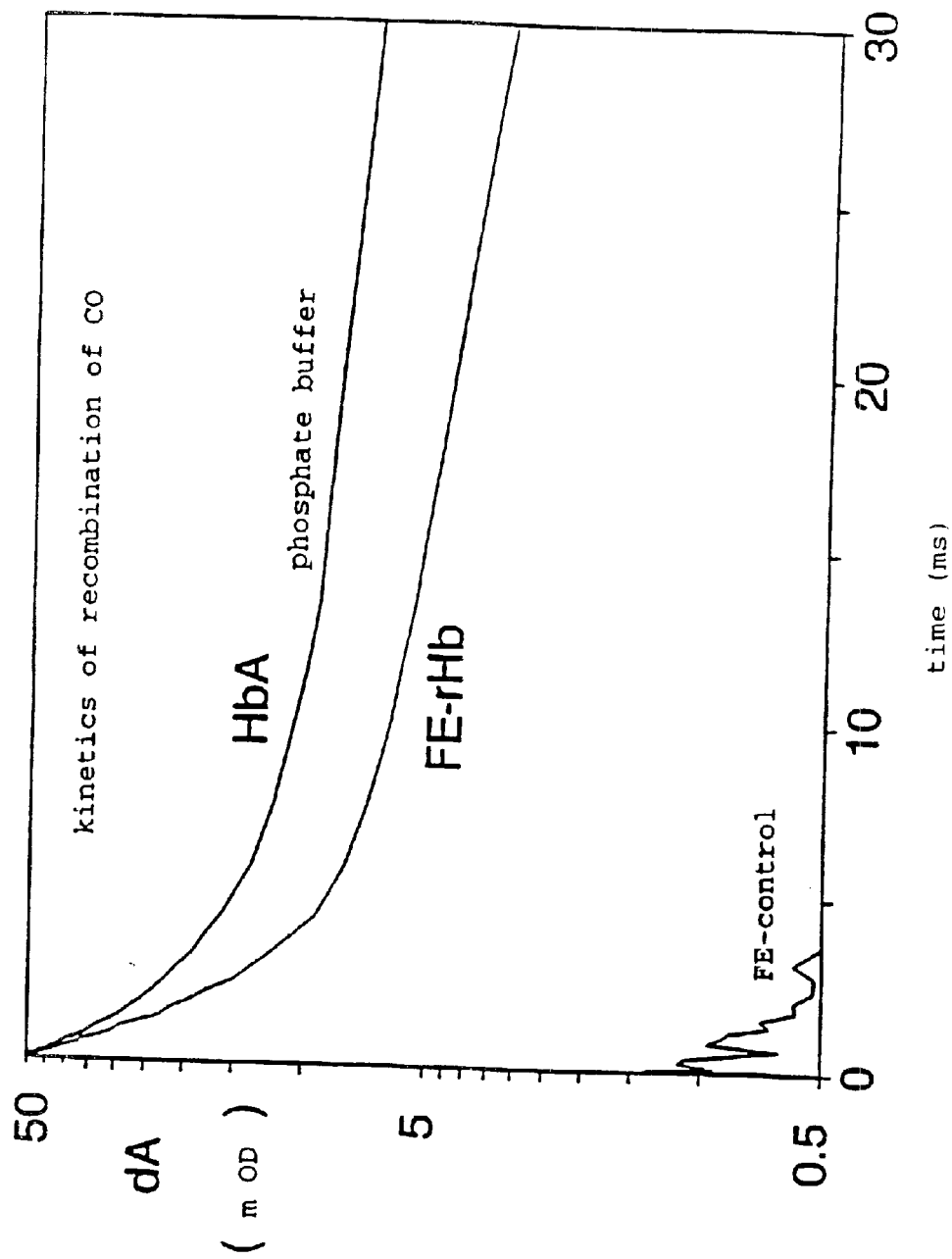

FIG. 9: Kinetics of recombination of CO with the FE-rHb fraction. The kinetics, following flash photolysis, is characteristic of the normal tetrameric Hb. The FE-Control fraction obtained from the control plants gives a signal of amplitude 1 mOD, that is to say about 50 times weaker than that observed for the FE-rHb fraction (48 mOD).

Figure 10:
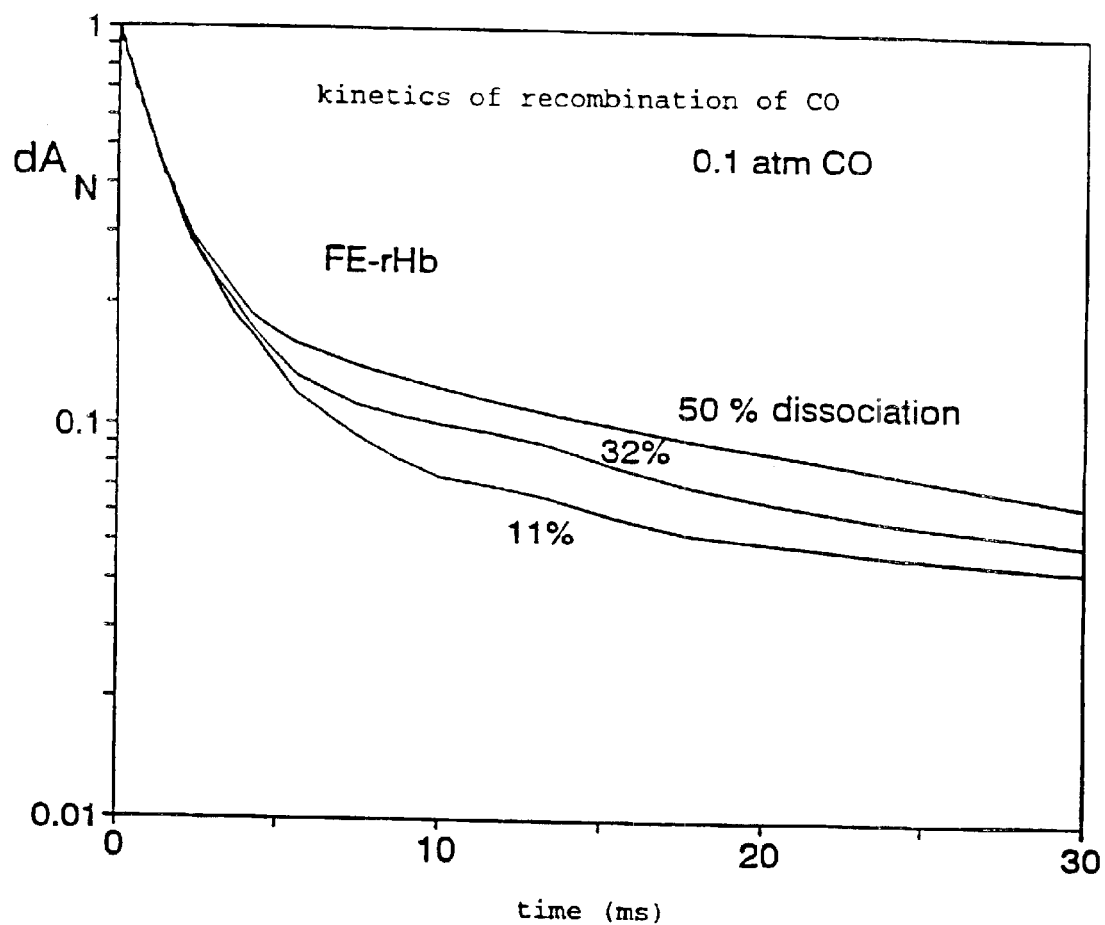

FIG. 10: Kinetics of recombination of CO with the FE-rHb fraction at various laser intensity levels. Similar results are observed for HbA (FIG. 6).

Figure 11:
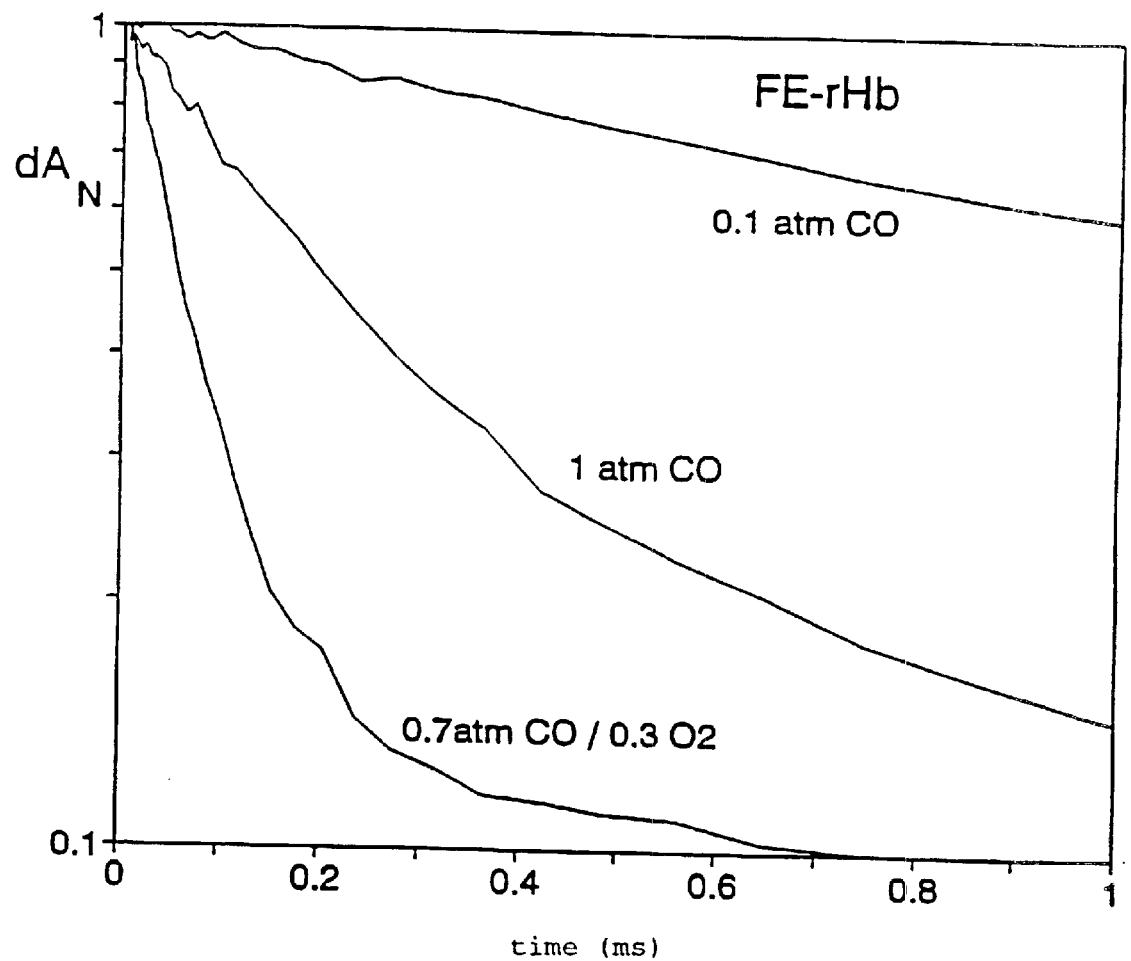

FIG. 11: Demonstration of the reversible binding of oxygen to the FE-rHb sample. Since the oxyhemoglobin samples give only weak signals, we used, for these measurements, the techniques of mixing a CO atmosphere and $O_2$. After photodissociation of CO, the rapid phase corresponds to the binding of oxygen. The oxygen is then replaced with CO which can again be photodissociated. The figure also shows the kinetics of recombination of the CO of the same sample equilibrated under 1 atm or 0.1 atm CO.

EXAMPLES

I. Construction of Basal Expression Binary Plasmids Allowing the Production of Recombinant Proteins in Tobacco Leaves The expression of genes in tobacco leaves requires the following regulatory sequences:

1) the constitutive double 35S promoter (pd35S) of CaMV (cauliflower mosaic virus). It corresponds to a duplication of the transcription-activating sequence situated upstream of the TATA element of the natural 35S promoter (Kay et al., 1987).

2) the sequence for termination of transcription, 35S polyA terminator, which corresponds to the noncoding 3' region of the sequence of the circular double-stranded DNA cauliflower mosaic virus producing the 35S transcript (Franck et al., 1980).

The constructions of the various plasmids via the use of recombinant DNA techniques (Sambrook et al., 1989) are derived from pBIOC4. This binary plasmid is derived from pGA492 (An, 1986) which contains, between the right and left borders derived from the plasmid pTiT37 of *Agrobacterium tumefaciens*, on its transfer DNA, the following sequences:

the constitutive promoter of the nos gene encoding nopaline synthase (Depicker et al., 1982), the coding sequence of the nptII gene encoding neomycin phosphotransferase II (Berg and Berg, 1983) deleted off the region of the first 8 codons including the ATG methionine initiation codon and fused to the sequence of the first 14 codons of the coding sequence of the nos gene (Depicker et al., 1982), the coding sequence of the nos gene lacking the region of the first 14 codons, the nos terminator (Depicker et al., 1982), a polylinker (HindIII-XbaI-SacI-HpaI-KpnI-ClaI-BglII) preceding the cat gene encoding chloramphenicol acetyltransferase (Close and Rodriguez, 1982) and the termination sequences of gene 6 of the plasmid pTiA6 *Agrobacterium tumefaciens* (Liu et al., 1993).

To remove virtually the whole of the coding sequence of the cat gene, the plasmid pGA492 was doubly digested with SacI (restriction site of the polylinker) and with ScaI (restriction site present in the sequence of the cat gene) and then subjected to the action of the enzyme T4 DNA polymerase (New England Biolabs) according to the manufacturer's recommendations. The ligation of the modified plasmid (20 ng) was carried out in a reaction medium of 10 µl containing 1 µl of 10× T4 DNA ligase buffer (Amersham) and 2.5 U of T4 DNA ligase enzyme (Amersham) at 14° C. for 16 hours. The *E. coli* DH5α bacteria previously made competent were transformed (Hanahan, 1983).

The plasmid DNA of the clones obtained, selected on 12 µg/ml tetracycline, was extracted according to the alkaline lysis method (Birnboim and Doly, 1979) and analyzed by enzymatic digestion with restriction enzymes. Next, the HindIII restriction site of the plasmid DNA of the selected clone was modified at an EcoRI restriction site with the aid of a phosphorylated HindIII-EcoRI adaptor (Stratagene Cloning Systems). To carry out this modification, 500 ng of plasmid DNA of the selected clone were digested with HindIII, dephosphorylated with the enzyme calf intestinal alkaline phosphatase (Boeringer Mannheim) according to the manufacturer's recommendations and coprecipitated in the presence of 1500 ng of HindIII-EcoRI adaptor DNA, ⅒ volume of 3 M sodium acetate pH 4.8 and 2.5 volumes of absolute ethanol at −80° C. for 30 min. After centrifugation at 12000 g for 30 min, the precipitated DNA was washed with 70% ethanol, dried, taken up in 8 µl of water, heated at 65° C. for 10 min, and then ligated in the presence of 1 µl of 10× T4 DNA ligase buffer (Amersham) and 2.5 U of the enzyme T4 DNA ligase (Amersham) at 14° C. for 16 hours. After inactivation of the T4 DNA ligase at 65° C. for 10 min, the ligation reaction mixture was digested with EcoRI, purified by electrophoresis on a 0.8% agarose gel, electroeluted (Sambrook et al., 1989), precipitated in the presence of ⅒ volume of 3 M sodium acetate pH 4.8 and 2.5 volumes of absolute ethanol at −80° C. for 30 min, centrifuged at 12000 g for 30 min, washed with 70% ethanol and then dried. The *E. coli* DH5α bacteria previously made competent were transformed (Hanahan, 1983). The plasmid DNA of the clones obtained, selected on 12 µg/ml tetracycline, was extracted according to the alkaline lysis method (Birnboim and Doly, 1979) and analyzed by enzymatic digestion with HindIII and EcoRI in particular. The resulting binary plasmid, which now possesses only the last 9 codons of the coding sequences of the cat gene and in which the EcoRI site is unique, was called pBIOC4.

a. Construction of the Expression Binary Plasmid pBIOC21

The expression cassette, consisting of the pd35S promoter and the 35S polyA terminator, was isolated from the plasmid pJIT163D. The plasmid pJIT163D is derived from the plasmid pJIT163 which is itself derived from the plasmid pJIT60 (Guerineau and Mullineaux, 1993). The plasmid pJIT163 possesses an ATG codon between the HindIII and SalI sites of the polylinker. To eliminate this ATG and to obtain the plasmid pJIT163D, the plasmid DNA pJIT163 was doubly digested with HindIII and SalI, purified by electrophoresis on a 0.8% agarose gel, electroeluted (Sambrook et al., 1989), precipitated in the presence of ⅒ volume of 3 M sodium acetate pH 4.8 and 2.5 volumes of absolute ethanol at −80° C. for 30 min, centrifuged at 12000 g for 30 min, washed with 70% ethanol, dried, subjected to the action of the Klenow enzyme (New England Biolabs) according to the manufacturer's recommendations, deproteinized by extraction with 1 volume of phenol:chloroform:isoamyl alcohol (25:24:1) and then 1 volume of chloroform:isoamyl alcohol (24:1), precipitated in the presence of ⅒ volume of 3 M sodium acetate pH 4.8 and 2.5 volumes of absolute ethanol at −80° C. for 30 min, centrifuged at 12000 g for 30 min, washed with 70% ethanol, dried and finally ligated in the presence of 1 µl of 10× T4 DNA ligase buffer (Amersham) and 2.5 U of T4 DNA ligase enzyme (Amersham) at 14° C. for 16 hours. The *E. coli* DH5α bacteria previously made competent, were transformed (Hanahan, 1983). The plasmid DNA of the clones obtained, selected on 50 µg/ml ampicillin, was extracted according to the alkaline lysis method (Birnboim and Doly, 1979) and analyzed by enzymatic digestion with restriction enzymes. To isolate the expression cassette consisting of the pd35S promoter and of the 35S polyA terminator (SacI-XhoI fragment), the plasmid DNA of the pJIT163D clone selected was digested with SacI and XhoI. The SacI-XhoI-fragment, carrying the expression cassette, was purified by electrophoresis on a 0.8% agarose gel, electroeluted (Sambrook et al., 1989) precipitated in the presence of ⅒ volume of 3 M sodium acetate pH 4.8 and 2.5 volumes of absolute ethanol at −80° C. for 30 min, centrifuged at 12000 g for 30 min, washed with 70% ethanol, dried and then subjected to the action of Mung Bean nuclease enzyme (New England Biolabs) according to the manufacturer's recommendations. This purified insert (200 ng) was cloned into the plasmid DNA of pBIOC4 (20 ng) digested with EcoRI, treated with the Mung Bean nuclease enzyme and dephosphorylated with the enzyme calf intestinal alkaline phosphatase (Boehringer Mannheim) according to the manufacturer's recommendations. The ligation reaction was carried out in 20 µl, in the presence of 2 µl of 10× T4 DNA ligase buffer (Amersham), 2 µl of 50% polyethylene glycol 8000 and 5 U of T4 DNA ligase enzyme (Amersham) at 14° C. for 16 hours. The *E. coli* DH5α bacteria previously made competent were transformed (Hanahan, 1983). The plasmid DNA of the clones obtained, selected on 12 µg/ml tetracyclin was extracted according to the alkaline lysis method (Birnboim and Doly, 1979) and analyzed by enzymatic digestion with restriction enzymes. The resulting plasmid was called pBIOC21.

b. Construction of the Co-Expression Binary Plasmid pBIOC43

The co-expression binary plasmid will allow expression of two genes in the same binary vector.

The co-expression binary plasmid is derived from pBIOC21. It contains two expression cassettes each consisting of a pd35S promoter and a 35S polyA terminator but differ in the polylinker separating the promoter from the terminator. One of the expression cassettes is that of pBIOC21 already described in paragraph I.a. The other expression cassette was obtained by replacing the HindIII-BamHI-SmaI-EcoRI polylinker of pJIT163D (described in paragraph I.a.) by a HindIII-EcoRI adaptor carrying the PacI, AscI, MluI, and HpaI restriction sites. This adaptor was obtained by renaturation of the 2 oligodeoxynucleotides WD11 (5' AGC TGA TTA ATT AAG GCG CGC CAC GCG TTA AC 3'; SEQ ID NO: 1) and WD12 (5' AAT TGT TAA CGC GTG GCG CGC CTT AAT TAA TC 3'; SEQ ID NO: 2) which are complementary for their 28 terminal 3' nucleotides. One hundred μM of each of these two oligodeoxynucleotides were previously phosphorylated by the action of 10 U of T4 polynucleotide kinase enzyme (New England Biolabs) in a total reaction volume of 10 μl of 10× T4 polynucleotide kinase buffer (New England Biolabs) and 3 μl of ATP (95 mM). The two reaction mixtures were incubated at 37° C. for 1 hour, and then at 65° C. for 20 min. They were then combined and their volume of phenol;chloroform:isoamyl alcohol (25:24:1) and 1 volume of chloroform:isoamyl alcohol (24:1), 50 μl of 3M sodium acetate pH 6.0 were added. The reaction mixture was incubated at 80° C. for 10 min and the cooled slowly to room temperature. The DNA was then precipitated in the presence of 2.5 volumes of absolute ethanol at −80° C. for 30 min, centrifuged at 14000 g at 4° C. for 1 hour, washed with 70% ethanol, centrifuged at 14000 g at 4° C. for 10 min, dried, taken up in 10 μl of H2O. The HindIII-EcoRI DNA fragment was then cloned at the HindIII-EcoRI sites of the plasmid DNA pJIT163D previously dephosphorylated with the enzyme calf intestinal alkaline phosphatase (New England Biolabs) according to the manufacturer's recommendations. The ligation reaction was carried out in a reaction volume of 20 μl in the presence of 1 U of T4 DNA ligase (Gibco-BRL) for a total DNA concentration of 8.5 nM with a vector/insert molar ratio of 1 and of 4 μl of 5× T4 DNA ligase buffer (Gibco-BRL) at 25° C. for 16 hours. The E. coli DH5□ bacteria previously made competent were transformed (Hanahan, 1985). The plasmid DNA of the clones obtained, selected on 100 μg/ml ampicillin, was extracted according to the alkaline lysis method (Stephen et al., 1990) and analyzed by enzymatic digestion. The resulting clone was called pBIOC42. Its validity was verified by sequencing with the aid of the "SEQUENASE™ Version 2.0 DNA Sequencing" kit marketed by United States Biochemical (USB) according to the dideoxynucleotides method (Sanger et al., 1977). The reaction condidtions follow the manufacturer's recommendations except for the denaturation and hybridization. The reaction medium containing the plasmid DNA (0.5 to 1 pmol), the oligonucleotide primer (2 pmol), 10% DMSO and 1× reaction buffer (USB), in incubated at 100° C. for 10 min, then suddenly cooled to −80° C. in dry ice.

From pBIOC42, the DNA fragment encoding the expression cassette consisting of the pd35S promoter and of the 35S polyA terminator was isolated by double digestion with SacI and XhoI. It was purified by electrophoresis on a 0.75% agarose gel, and then subjected to the action of the "GENECLEAN™ II" kit marketed by BIO101 according to the manufacturer's recommendation. Next, this DNA fragment was inserted at the SacI and XhoI sites of the plasmid pBCSK+ marketed by Stratagene and previously dephosphorylated with the enzyme calf intestinal alkaline phosphatase (New England Biolabs) according to the manufacturer's recommendations. The ligation was carried out in a reaction volume of 20 μl in the presence of 1 U of T4 DNA ligase (Gibco-BRL) for a total DNA concentration of 8.5 nm with a vector/insert molar ratio of 1 and of 4 μl of 5× T4 DNA ligase buffer (Gibco-BRL) at 25° C. for 16 hours. The E. coli DH5α bacteria previously made competent were transformed (Hanahan, 1985). The plasmid DNA of the clones obtained, selected on 30 μg/ml of chloramphenicol, was extracted according to the alkaline lysis method (Stephen et al., 1990) and analyzed by enzymatic digestion with restriction enzymes. The resulting plasmid was called pBIOC75.

From pBIOC75, the DNA fragment carrying the expression cassette consisting of the pd35S promoter and the 35S polyA terminator was isolated by digestion with KpnI. It was purified by electrophoresis on a 0.75% agarose gel, and then subjected to the action of the "GENECLEAN™ II" kit marketed by BIO101 according to the manufacturer's recommendations. Next, this DNA fragment was ligated to the plasmid DNA of pBIOC21 digested with KpnI and dephosphorylated with the enzyme calf intestinal alkaline phosphatase (New England Biolabs) according to the manufacturer's recommendations. The ligation was carried out in a reaction volume of 20 μl in the presence of 1 U of T4 DNA ligase (Gibco-BRL) for a total DNA concentration of 8.5 nM with a vector/insert molar ratio of 1 and of 4 μl of 5× T4 DNA ligase buffer (Gibco-BRL) at 25° C. for 16 hours. The E. coli DH5α bacteria previously made competent were transformed (Hanahan, 1985). The plasmid DNA of the clones obtained, selected on 12 μg/ml of tetracycline, was extracted according to the alkaline lysis method (Stephen et al., 1990) and analyzed by enzymatic digestion with restriction enzymes. The resulting plasmid was called pBIOC43.

II. Construction of the Chimeric Genes Encoding the α and β Globin Chains Allowing Expression of Recombinant Human Hemoglobin in the Cytoplasm of Tobacco Leaves The plasmid alpha1pJW101 contains the cDNA for the α globin chain, cloned into the plasmid pMB9 as described by Wilson et al. (1978).

The M13mp10 phage cIIIX beta contains the cDNA for the β globin chain, cloned into the M13 mp10 phage as described by Nagai et al. (1985). In this construction, the cDNA encoding β globin was inserted in 3' of the coding sequence for the cII protein of the lambda phage, followed by that encoding the FX tetrapeptide, forming a fusion gene in which the initiator ATG codon of β globin has been deleted.

a. Construction of the Plasmid pBIOC44 Containing the cDNA Encoding α Globin for Cytoplasmic Targeting To obtain cytoplasmic targeting of the α globin chain, the initiator methionine codon of the α globin chain was maintained.

The cDNA encoding the cytoplasmic targeting α globin chain was obtained in three stages. The first two stages made it possible to suppress the internal HindIII site (substitution of a T for a C) at position 276 of the coding sequence whereas the third stage combines the 2 cDNA fragments encoding the recombinant α globin chain.

The first stage consisted in the amplification of the first 95 codons of the mature □ globin chain on the plasmid alpha1pJW101 with the aid of the 2 oligodeoxynucleotides, WD13 (5' tacaagcttaaca ATG GTG CTG TCT CCg GCC GAC 3'; SEQ ID NO: 3) and AD27 (5' CGG GTC CAC CCC GAG CTT GTG 3'; SEQ ID NO: 4). The WD13 primer provides the HindIII restriction site, the sequence aaca favoring the initiation of translation (Joshi, 1987) and preceding the initiator ATG codon followed by the first 6 codons of the mature □ globin chain of which the fourth (CCT) is substituted for CCg (silent mutation) in order to create the EagI restriction site. The AD27 primer allows the suppresion of the HindIII restriction site by substitution of nucleotide T for C (position 276 of the coding sequence. The PCR amplification was carried out in 100 µl of reaction medium containing 10 µl of 10× Taq DNA polymerase buffer (100 mM Tris-HCl pH 8.4, 500 mM KCl and 20 mM MgCl$_2$), 16 µl of the dNTP mixture (1.25 mM dATP, 1.25 mM dCTP, 1.25 mM dGTP and 1.25 mM dTTP), 10 µl of each of the primers described above at 10 µl, 10 µl of template DNA (alpha1pJW101) at 1 ng/µl and 0.5 µl of Taq DNA polymerase at 5 U/µl (Perkin Elmer). Thirty cycles each comprising 30 sec of denaturation at 97° C., 1 min hybridization at 55° C. and 2 min extension at 72° C. were carried out in the Appligène "CROCODILE™ II" apparatus. The amplified DNA fragments were then purified by electrophoresis on a 1.8% agarose gel and by the action of the "GENECLEAN™ II" kit marketed by BIO101 according to the manufacturer's recommendations. The purified amplified DNA fragments are taken up in 20 µl.

The second stage consisted in the amplification of the last 54 codons of the mature □ globin chain on the plasmid alpha1pJW101 with the aid of the 2 oligodeoxynucleotides, AD26 (5' CAC AAG CTC CGG GTG GAC CCG 3'; SEQ ID NO: 5) and WD14 (5' gcgaattc TCA ACG GTA TTT GGA GGT CAG CAC 3'; SEQ ID NO: 6). The WD14 primer provides the EcoRI restriction site situated just after the stop codon. The AD26 primer allows the suppression of the HindIII restriction site by substitution of nucleotide T for C (position 276 of the coding sequence). The PCR amplification was carried out as described in the first stage. The treatment of the amplified DNA fragments was carried out as described in the first stage.

The third stage was the PCR amplification of the complete cDNA encoding the α globin chain (142 codons including the initiator ATG). The two types of DNA fragments amplified in the first and second stages served as template DNA and the two primers used were WD13 and WD14. The PCR amplification was carried out as described in the first stage except that the hybridization temperature of the cycle is 60° C. The amplified DNA fragments were then extracted with H$_2$O-saturated ether after having adjusted the volume to 500 µl with TE buffer (10 mM Tris-HCl pH 8.0, 1 mM EDTA). After extraction with 1 volume of phenol:chloroform:isoamyl alcohol (25:24:1) and 1 volume of chloroform:isoamyl alcohol (24:1), the DNA fragments were precipitated in the presence of ⅒ volume of 3 M sodium acetate pH 6.0 and 2 volumes of absolute ethanol at −80° C. for 30 min, centrifuged at 14000 g at 4° C. for 30 min, washed with 70% ethanol, centrifuged at 14000 g at 4° C. for 10 min, dried, taken up in 50 µl of H$_2$O. Next, 25 µl of these DNA fragments were doubly digested with HindIII and EcoRI, purified by electrophoresis on 1.8% agarose gel and by the action of the "Geneclean II" kit (BIO101) and cloned at the HindIII and EcoRI sites of the plasmid pNEB193 marketed by New England Biolabs, and previously dephosphorylated with the enzyme calf intestinal alkaline phosphatase (New England Biolabs) according to the manufacturer's recommendations. The ligation and the transformation were carried out as described in section I.b. The plasmid DNA of the clones obtained, selected on 100 µg/ml ampicillin, was extracted according to the alkaline lysis method (Stephen et al., 1990) and analyzed by enzymatic digestion. The resulting clone was called pBIOC44. The nucleotide sequence of the cDNA encoding the recombinant α globin chain was verified by sequencing with the aid of the "Sequenase Version 2.0 DNA Sequencing" kit marketed by United States Biochemical (USB) as described in section I.b. The sequencing revealed two silent mutations situated at the forty-eighth nucleotide (C modified to T) and at the fifty-fourth (T modified to C) of the coding sequence for the α globin chain.

b. Construction of the Plasmid pBIOC45 Containing the cDNA Encoding β Globin for Cytoplasmic Targeting To obtain cytoplasmic targeting of the β globin chain, the methionine codon was fused with the first codon of the mature β globin chain by maintaining the open reading frame since ATG had been deleted from the construct M13mp10 cIIFX beta.

The cDNA encoding the cytoplasmic targeting β globin chain was obtained by the PCR amplification of the 146 codons constituting the mature β globin chain on the phage M13mp10 cIIFX beta with the aid of the 2 oligodeoxynucleotides WD15 (5' gtcattaattaaca ATG GTG CAC CTG ACT CCT GAG GAG AAG TCg GCC GTT AC 3'; SEQ ID NO: 7) and WD16 (5' aatgagctcgttaacgcgt TTA GTG ATA CTT GTG GGC CAG GGC 3'; SEQ ID NO: 8). The WD15 primer provides the PacI restriction site, the aaca sequence favoring the initiation of translation (Joshi, 1987) and the initiator ATG codon followed by the first 12 codons of the mature β globin chain of which the ninth (TCT) is substituted for TCg (silent mutation) in order to create the EagI restriction site. The WD16 primer provides the MluI, HpaI, and SacI restriction sites placed after the stop codon. The PCR amplification and the treatment of the amplified DNA fragments were carried out as described in the third stage of section II.a. Next, 25 µl of these DNA fragments were doubly digested with PacI and SacI, purified by electrophoresis on a 1.8% agarose gel and by the action of the "GENECLEAN™ II" kit (BIO101) and cloned at the PacI and SacI sites of the plasmid pNEB193 marketed by New England Biolabs, previously dephosphorylated by the enzyme calf intestinal alkaline phosphatase (New England Biolabs) according to the manufacturer's recommendations. The ligation and the transformation were carried out as described in section I.b. The plasmid DNA of the clones obtained, selected on 100 µg/ml ampicillin, was extracted according to the alkaline lysis method (Stephen et al., 1990) and analyzed by enzymatic digestion. The resulting clone was called pBIOC45. The nucleotide sequence of the cDNA encoding the recombinant β globin chain was verified by sequencing as described in section I.b.

c. Construction of the Expression Binary Plasmids pBIOC46 and pBIOC47, and of the Co-Expression Binary Plasmid pBIOC49 for Cytoplasmic Targeting c.1. Construction of the Binary Plasmid pBIOC46 Containing cDNA Encoding α Globin for Cytoplasmic Targeting Starting with pBIOC44, the HindIII-EcoRI fragment carrying the cDNA encoding the cytoplasmic targeting α globin chain was isolated by double enzymatic digestion with HindIII and EcoRI, purified by electrophoresis on a 1.8% agarose gel and by the action of the "GENECLEAN™ II" kit (BIO101). Next, this DNA fragment was ligated with the plasmid DNA of pBIOC21 doubly digested with HindIII and EcoRI, and dephosphorylated with the enzyme calf intestinal alkaline phosphatase (New England Biolabs) according to the manufacturer's recommendations. The ligation and the transformation were carried out as described in section I.b. The plasmid DNA of the clones obtained, selected on 10 µg/ml tetracycline, was extracted according to the alkaline lysis method (Stephen et al., 1990) and analyzed by enzymatic digestion. The resulting clone was called pBIOC46. The nucleotide sequence of the cDNA encoding the recombinant α globin chain was verified by sequencing as described in section I.b. The plasmid DNA of the binary vector pBIOC46 was introduced by direct transformation into the *Agrobacterium tumefaciens* LBA4404 strain according to the method of Holsters et al. (1978). The validity of the clone selected was verified by enzymatic digestion of the plasmid DNA introduced.

c.2. Construction of the Binary Plasmid pBIOC47 Containing the cDNA Encoding β Globin for Cytoplasmic Targeting Starting with pBIOC45, HindIII-EcoRI fragment carrying the cDNA encoding the cytoplasmic targeting β globin chain was isolated by double enzymatic digestion with HindIII (total digestion) and EcoRI (partial digestion), purifies by electrophoresis on a 1.8% agarose gel and by the action of the "GENECLEAN™" kit (BIO101). Next, this DNA fragment was ligated with the plasmid DNA of pBIOC21 digested with HindIII and EcoRI and dephosphorylated with the enzyme calf intestinal alkaline phosphatase (New England Biolabs) according to the manufacturer's recommendations. The ligation and the transformation were carried out as described in section I.b.

The plasmid DNA of the clones obtained, selected on 10 μg/ml tetracycline, was extracted according to the alkaline lysis method (Stephen et al., 1990) and analyzed by enzymatic digestion. The resulting clone was called pBICO47. The nucleotide sequence of the cDNA encoding the recombinant β globin chain was verified by sequencing as described in section I.b. The plasmid DNA of the binary vector pBIOC47 was introduced by direct transformation into the *Agrobacterium tumefaciens* LBA4404 strain according to the method of Holsters et al. (1978). The validity of the clone selected was verified by enzymatic digestion of the plasmid DNA introduced.

c.3. Construction of the Co-Expressing Binary Plasmid pBIOC49 Containing the cDNA Encoding the α and β Globins for Cytoplasmic Targeting The HindIII-EcoRI fragment carrying the cDNA encoding the cytoplasmic targeting α globin chain was isolated from pBIOC44 described in section II.c.1., and ligated with the plasmid DNA of pBIOC43 doubly digested with HindIII and EcoRI, and previously dephosphorylated with the enzyme calf intestinal alkaline phosphatase (New England Biolabs) according to the manufacturer's recommendations. The ligation and the transformation were carried out as described in section I.b. The plasmid DNA of the clones obtained, selected on 12 μg/ml tetracycline, was extracted according to the alkaline lysis method (Stephen et al., 1990) and analyzed by enzymatic digestion. The resulting clone was called pBIOC48.

The PacI-MluI fragment carrying the cDNA encoding the cytoplasmic targeting β globin chain was isolated from pBIOC45 described in section II.c.2., and ligated with the plasmid DNA of pBIOC48 doubly digested with PacI and MluI, and dephosphorylated by the enzyme calf intestinal alkaline phosphatase (New England Biolabs) according to the manufacturer's recommendations. The ligation and the transformation were carried out as described in section I.b., except that the *E. coli* Sure tet⁻ strain was used in place of DH5α. The Sure tet⁻ strain is derived from the Sure strain (Stratagene) made sensitive to tetracycline by the loss of the F' episome. The plasmid DNA of the clones obtained, selected on 10 μg/ml tetracycline, was extracted according to the alkaline lysis method (Stephen et al., 1990) and analyzed by enzymatic digestion. The resulting clone was called pBIOC49.

The nucleotide sequence of the cDNAs encoding the recombinant α and β globin chains was verified by sequencing as described in section I.b. The plasmid DNA in the binary vector pBIOC49 was introduced by direct transformation into the *Agrobacterium tumefaciens* LBA4404 strain according to the method of Holsters et al. (1978). The validity of the clone selected was verified by enzymatic digestion of the plasmid DNA introduced.

III. Construction of the Chimeric Genes Encoding the α and β Globin Chains Allowing Expression of Recombinant Human Hemoglobin in the Mitochondria of Tobacco Leaves To obtain mitochondrial targeting, the sequence encoding the transit peptide of the *Nicotiana plumbaginifolia* mitochondrial ATPase-Fi β subunit precursor (ATG GCT TCT CGG AGG CTT CTC GCC TCT CTC CTC CGT CAA TCG GCT CAA CGT GGC GGC GGT CTA ATT TCC CGA TCG TTA GGA AAC TCC ATC CCT AAA TCC GCT TCA CGC GCC TCT TCA CGC GCA TCC CCT AAG GGA TTC CTC TTA AAC CGC GCC GTA CAG TAC; SEQ ID NO: 9) is fused with the first codon of the sequence encoding, on the one hand, the mature α globin chain (deletion of the initiator ATG) and, on the other hand, the mature β globin chain (deletion of the initiator ATG) while maintaining the open reading frames.

The sequence encoding the *Nicotiana plumbaginifolia* mitochondrial ATPase F1 β subunit is contained in the plasmid pTZ-catp2-1 provided by Boutry. This plasmid corresponds to the plasmid pTZ18R containing the cDNA (cNP10) as described by Boutry and Chua (1985).

The N-terminal transit peptide, composed of 54 amino acids as defined by Chaumont et al. (1994), was used during the carrying out of the constructions.

a. Construction of the Plasmid pBIOC50 Containing the cDNA Encoding α Globin for Mitochondrial Targeting To obtain mitochondrial targeting of the α globin chain, the sequence encoding the transit peptide of the *Nicotiana plumbaginifolia* mitochondrial ATPase-F1 β subunit precursor was fused with the first codon of the sequence encoding the mature α globin chain while maintaining the open reading frame. The cleaving sequence between the sequences of the transit peptide and the mature α globin chain is Tyr-Val.

The sequence encoding the transit peptide of the mitochondrial ATPase-F1 □ subunit precursor was amplified by PCR on the plasmid pTZ-catp2-1 with the aid of the 2 oligodeoxynucleotides, WD17 (5' cgcaagcttaaca ATG GCT TCT CGG AGG CTT CTC 3'; SEQ ID NO: 10) and WD18 (5' tag aat tC GGC cGG AGA CAG CAC GTA CTG TAC GGC GCG GTT TAA G 3'; SEQ ID NO: 11). The WD17 primer provides the HindIII restriction site, the aaca sequence promoting the initiation of translation (Joshi, 1987) and the first 7 codons of the transit peptide (including the initiator ATG). The WD18 primer provides the EcoRI restriction site, the first 5 codons of the sequence encoding the mature α globin chain (an EagI restriction site is created by silent mutation in the fourth codon (CCT modified to CCG) and the last 7 codons of the sequence of the transit peptide. PCR amplification and the treatment of the amplified DNA fragments were carried out as described in the third step of chapter II.a. Next, these DNA fragments were doubly digested with HindIII and EagI, purified by electrophoresis on a 1.8% agarose gel and by the action of the "GENECLEAN™ II" kit (BIO101) and cloned at the HindIII and EagI sites of the plasmid pBIOC44 described in section II.a., previously purified by electrophoresis on a 0.7% agarose gel and using the "GENECLEAN™ II" kit. The plasmid pBIOC44 was dephosphorylated by the enzyme calf intestinal alkaline phosphatase (New England Biolabs) according to the manufacturer's recommendations. The ligation and the transformation were carried out as described in section I.b. The plasmid DNA of the clones obtained, selected on 100 μg/ml ampicillin, was extracted according to the alkaline lysis method (Stephen et al., 1990) and analyzed by enzymatic digestion. The resulting clone was called pBIOC50. The nucleotide sequence of this chimeric gene resulting from the translational fusion between the sequence encoding the transit peptide and the cDNA encoding the mature α globin chain was verified by sequencing as described in section I.b. The sequencing revealed two silent mutations situated at the tenth nucleotide (C modified to A) and at the one hundred forty first (C modified to G) of the coding sequence for the transit peptide.

b. Construction of the Plasmid pBIOC51 Containing the cDNA Encoding β Globin for Mitochondrial Targeting To obtain mitochondrial targeting of the β globin chain, the sequence encoding the transit peptide of the *Nicotiana plumbaginifolia* mitochondrial ATPase-F1 β subunit precursor was fused with the first codon of the sequence encoding the mature β globin chain while maintaining the open reading frame. The cleaving sequence between the sequences of the transit peptide and the mature β globin chain is Tyr-Val.

The sequence encoding the transit peptide of the mitochondrial ATPase-F1 □ subunit precursor was amplified by PCR on the plasmid pTZ-catp2-1 with the aid of the 2 oligodeoxynucleotides, WD19 (5' gtcattaattaaca ATG GCT TCT CGG AGG CTT CTC GCC TCT C 3'; SEQ ID NO: 12) and WD20 (5'aatgagct C GGC cGA CTT CTC CTC AGG AGT CAG GTG CAC GTA CTG TAC GGC GCG GTT TAA G 3'; SEQ ID NO: 13). The WD19 primer provides the PacI restriction site, the aaca sequence promoting the initiation of translation (Joshi, 1987) and preceding the first 9 codons of the transit peptide (including the initiatior ATG). The WD20 primer provides the SacI restriction site, the first 10 codons of the sequence encoding the mature β globin chain (an EagI restriction site is created by silent mutation in the ninth condon (TCT modified to TCg)) and the last 7 codons of the sequence of the transit peptide. The PCR amplification and the treatment of the amplified DNA fragments were carried out as described in the third stage of section II.a. Next, these DNA fragments were doubly digested with PacI and EagI, purified by electrophoresis on a 1.8% agarose gel and by the action of the "GENECLEAN™ II" kit (BIO101)and cloned at the PacI and EagI sites of the plasmid pBIOC45 described in section II.b., previously purified by electrophoresis on a 0.75% agarose gel and using "GENECLEAN™ II" kit. The plasmid pBIOC45 was dephosphorylated by the enzyme calf intestinal alkaline phosphatase (New England Biolabs) according to the manufacturer's recommendations. The ligation and the transformation were carried out as described in section I.b. The plasmid DNA of the clones obtained, selected on 100 μg/ml ampicillin, was extracted according to the alkaline lysis method (Stephen et al., 1990) and analyzed by enzymatic digestion. The resulting clone was called pBIOC51. The nucleotide sequence of this chimeric gene resulting from the translational fusion between the sequence encoding the transit peptide and the cDNA encoding the mature β globin chain was verified by sequencing as described in section I.b.

c. Construction of the Co-Expression Binary Plasmid pBIOC53 Containing the cDNAs Encoding the α and β Globins, for Mitochondrial Targeting The HindIII-EcoRI fragment carrying the cDNA encoding the mitochondrial targeting α globin chain was isolated from pBIOC50 described in section III.a., and ligated to the plasmid DNA of pBIOC43 doubly digested with HindIII and EcoRI, and dephosphorylated by the enzyme calf intestinal alkaline phosphatase (New England Biolabs) according to the manufacturer's recommendations. The ligation and the transformation were carried out as described in section I.b. The plasmid DNA of the cones obtained, selected on 10 μg/ml tetracycline, was extracted according to the alkaline lysis method (Stephen et al., 1990) and analyzed by enzymatic digestion. The resulting clone was called pBIOC52.

The PacI-MluI fragment carrying the cDNA encoding the mitochondrial targeting β globin chain was isolated from pBIOC51 described in section III.b., and ligated to the plasmid DNA of pBIOC52 doubly digested with PacI and MluI, and dephosphorylated by the enzyme calf intestinal alkaline phosphatase (New England Biolabs). The ligation and the transformation were carried out as described in section II.c.3 using the *E. coli* Sure tet⁻ strain. The plasmid DNA of the clones obtained, selected on 10 μg/ml tetracycline, was extracted according to the alkaline lysis method (Stephen et al., 1990) and analyzed by enzymatic digestion. The resulting clone was called pBIOC53.

The nucleotide sequence of the cDNAs encoding the recombinant α and β globin chains allowing α mitochondrial targeting was verified by sequencing as described in section I.b. The plasmid DNA of the binary vector pBIOC53 was introduced by direct transformation into the *Agrobacterium tumefaciens* LBA4404 strain according to the method of Holsters et al. (1978). The validity of the clone obtained was verified by enzymatic digestion of the plasmid DNA introduced.

IV. Construction of the Chimeric Genes Encoding the α and β Globin Chains Allowing Expression of Recombinant Human Hemoglobin in the Chloroplasts of Tobacco Leaves To obtain chloroplastic targeting, the sequence encoding the transit peptide of the precursor of the small subunit of ribulose 1,5-diphosphate carboxylase of *Pisum sativum* L. (ATG GCT TCT ATG ATA TCC TCT TCA GCT GTG ACT ACA GTC AGC CGT GCT TCT ACG GTG CAA TCG GCC GCG GTG GCT CCA TTC GGC GGC CTC AAA TCC ATG ACT GGA TTC CCA GTT AAG AAG GTC AAC ACT GAC ATT ACT TCC ATT ACA AGC AAT GGT GGA AGA GTA AAG TGC; SEQ ID NO: 14) is fused with the first codon of the sequence encoding, on the one hand, the mature α globin chain (deletion of the initiator ATG) and, on the other hand, the mature β globin chain (deletion of the initiatior ATG) while maintaining the open reading frames.

This N-terminal transit peptide, composed of 57 amino acids, as defined by Anderson et al. (1986), was insolated from the plasmid pJIT117 (Guerineau et al., 1988) and used during the carrying out of the constructions.

a. Construction of the Plasmid pBIOC55 Containing the cDNA Encoding α Globin for Chloroplast Targeting To obtain chloroplast targeting of the α globin chain, the sequence encoding the transit peptide of the precursor of the small subunit of the ribulose 1,5-diphosphate carboxylase of *Pisum sativum* L. was fused with the first codon of the sequence encoding the mature α globin chain while maintaining the open reading frame. The cleaving sequence between the sequences of the transit peptide and of the mature α globin chain is Cys-Val.

The sequence of the transit of the precursor of the small subunit of ribulose 1,5-diphosphate carboxylase was amplified by PCR on the plasmid pJIT117 with the aid of the 2 oligodeoxynucleotides, WD21 (5' cgcaagcttaaca ATG GCT TCT ATG ATA TCC TCT TCA GC 3'; SEQ ID NO: 15) and WD22 (5' tag aat tC GGC cGG AGA CAG CAC GCA CTT TAC TCT TCC ACC ATT GC 3'; SEQ ID NO: 16). The WD21 primer provides the HindIII restriction site, the aaca sequence promoting the initiation of translation (Joshi, 1987) and the first 8 codons of the transit peptide (including the initiator ATG). The WD22 primer provides the EcoRI restriction site, the first 5 codons of the sequence encoding the mature α globin chain (an EagI restriction site is created by silent mutation in the fourth codon (CCT modified to CCg)) and the last 7 codons of the sequence of the transit peptide. The PCR amplification and the treatment of the amplified DNA fragments were carried out as described in the third stage of section II.a.

Next, these DNA fragments were doubly digested with HindIII and EcoRI and cloned at the HindIII and EcoRI sites of the plasmid pNEB193 marketed by New England Biolabs. The plasmid pNEB 193 was dephosphorylated as described in II.a. The ligation and the transformation were carried out as described in section I.b. The plasmid DNA of the clones obtained, selected on 100 μg/ml ampicillin, was extracted according to the alkaline lysis method (Stephen et al., 1990) and analyzed by enzymatic digestion. The resulting clone was called pBIOC54. The nucleotide sequence of this chimeric gene resulting from the translational fusion between the sequence encoding the transit peptide and the cDNA encoding the mature α globin chain was verified by sequencing as described in section I.b.

From the plasmid pBIOC54, the HindIII-EagI fragment, carrying the sequence encoding the transit peptide of the precursor of the small subunit of ribulose 1,5-diphosphate carboxylase and the first 4 codons of the mature α globin chain was isolated by double digestion, HindIII (total digestion) and EagI (partial digestion). This HindIII-EagI fragment, purified by electrophoresis on a 1.8% agarose gel and by the action of the "GENECLEAN™ II" kit (BIO101) was cloned at the HindIII and EagI sites of the dephosphorylated plasmid pBIOC44 as described in section II.a. The ligation and the transformation were carried out as described in section I.b. The plasmid DNA of the clones obtained, selected on 100 μg/ml ampicillin, was extracted according to the alkaline lysis method (Stephen et al., 1990) and analyzed by enzymatic digestion. The resulting clone was called pBIOC55. The nucleotide sequence of this chimeric gene resulting from the translational fusion between the sequence encoding the transit peptide and the cDNA encoding the mature α globin chain was verified by sequencing as described in section I.b.

b. Construction of the Plasmid pBIOC57 Containing the cDNA Encoding β Globin for Chloroplast Targeting To obtain chloroplast targeting of the β globin chain, the sequence encoding the transit peptide of the *Pisum sativum* L. ribulose 1,5-diphosphate carboxylase small subunit precursor was fused with the first codon of the sequence encoding the mature β globin chain while maintaining the open reading frame. The cleaving sequence between the sequences of the transit peptide and the mature β globin chain is Cys-Val.

The sequence encoding the transit peptide of the ribulose 1,5-diphosphate carboxylase small subunit precursor was amplified by PCR on the plasmid pJIT117 with the aid of the 2 oligodeoxynucleotides, WD23 (5' gtcattaattaaca ATG GCT TCT ATG ATA TCC TCT TCA GCT GTG 3'; SEQ ID NO: 17) and WD24 (5' aatgagct C GGC cGA CTT CTC CTC AGG AGT CAG GTG CAC GCA CTT TAC TCT TCC ACC 3'; SEQ ID NO: 18). The WD23 primer provides the PacI restriction site, the aaca sequence promoting the initiation of translation (Joshi, 1987) and preceding the first 10 codons of the transit peptide (including the initiator ATG). The WD24 primer provides the SacI restriction site, the first 10 codons of the sequence encoding the mature β globin chain (an EagI restriction site is created by silent mutation in the ninth codon (TCT modified to TCg)) and the last 6 codons of the sequence of the transit peptide. The PCR amplification and the treatment of the amplified DNA fragments were carried out as described in the third stage of section II.a. Next, these DNA fragments were doubly digested with PacI and SacI, purified by electrophoresis on a 1.8% agarose gel and by the action of the "GENECLEAN™ II" kit (BIO101) and cloned at the PacI and SacI sites of the plasmid pNEB193 marketed by New England Biolabs. The plasmid pNEB193 was dephosphorylated as described in II.a. The ligation and the transformation were carried out as described in section I.b. The plasmid DNA of the clones obtained, selected on 100 μg/ml ampicillin, was extracted according to the alkaline lysis method (Stephen et al., 1990) and analyzed by enzymatic digestion. The resulting clone was called pBIOC56. The nucleotide sequence of this chimeric gene resulting from the translational fusion between the sequence encoding the transit peptide and the cDNA encoding the mature β globin chain was verified by sequencing as described in section I.b.

From the plasmid pBIOC56, the PacI-EagI fragment, carrying the sequence of the transit peptide of the ribulose 1,5-diphosphate carboxylase small subunit precursor and the first 9 codons of the sequence encoding the mature β globin chain, was isolated by double digestion, PacI (total digestion) and EagI (partial digestion). This PacI-EagI fragment, purified by electrophoresis on a 1.8% agarose gel and by the action of the "GENECLEAN™ II" kit (BIO101), was cloned at the PacI and EagI sites of the dephosphorylated plasmid pBIOC45 as described in section II.a. The ligation and the transformation were carried out as described in section I.b. The plasmid DNA of the clones obtained, selected on 100 μg/ml ampicillin, was extracted according to the alkaline lysis method (Stephen et al., 1990), and analyzed by enzymatic digestion. The resulting clone was called pBIOC57. The nucleotide sequence of this chimeric gene resulting from the translational fusion between the sequence encoding the transit peptide and the cDNA encoding the mature β globin chain was verified by sequencing as described in section I.b.

c. Construction of the Co-Expression Binary Plasmid pBIOC59 Containing the cDNAs Encoding the α and β Globins, for Chloroplast Targeting The HindIII-EcoRI fragment carrying the cDNA encoding the chloroplast targeting α globin chain was isolated from pBIOC55 described in section IV.a., and ligated to the plasmid DNA of pBIOC43 doubly digested with HindIII and EcoRI and dephosphorylated as described in II.a. The ligation and the transformation were carried out as described in section I.b. The plasmid DNA of the clones obtained, selected on 10 μg/ml tetracycline, was extracted according to the alkaline lysis method (Stephen et al., 1990) and analyzed by enzymatic digestion. The resulting clone was called pBIOC58.

The PacI-MluI fragment carrying the cDNA encoding the chloroplast targeting β globin chain was isolated from pBIOC57 described in section IV.b., and ligated to the plasmid DNA of pBIOC58 doubly digested with PacI and MluI, and dephosphorylated as described in II.a. The ligation and the transformation were carried out as described in section II.c.3 suing the *E. coli* Sure tet⁻ strain. The plasmid DNA of the clones obtained, selected on 10 μg/ml tetracycline, was extracted according to the alkaline lysis method (Stephen et al., 1990) and analyzed by enzymatic digestion. The resulting clone was called pBIOC59.

The nucleotide sequence of the cDNAs encoding the recombinant α and β globin chains allowing chloroplast targeting was verified by sequencing as described in section I.b. The plasmid DNA of the binary vector pBIOC59 was introduced by direct transformation into the *Agrobacterium tumefaciens* LBA4404 strain according to the method of Holsters et al. (1978). The validity of the clone selected was verified by enzymatic digestion of the plasmid DNA introduced.

V. Construction of the Chimeric Genes Encoding the α and β Globin Chains Allowing Expression of the Recombinant Human Hemoglobin for Secretion in Tobacco Leaves To obtain secretion, the sequence encoding the signal peptide (SP) of sporamine A of the tuberized roots of sweet potato (Murakami et al., 1986; Matsuoka and Nakamura, 1991) (ATG AAA GCC TTC ACA CTC GCT CTC TTC TTA GCT CTT TCC CTC TAT CTC CTG CCC AAT CCA GCC CAT TCC; SEQ ID NO: 19), is fused with the first codon of the sequence encoding, on the one hand, the mature α globin chain (deletion of the initiator ATG) and, on the other hand, the mature β globin chain (deletion of the initiator ATG) while maintaining the open reading frames. This signal peptide of 23 amino acids was isolated from the plasmid pMAT103 (Matuoka and Nakamura, 1991) and used during the carrying out of the constructions.

a. Construction of the Plasmid pBIOC60 Containing the cDNA Encoding α Globin for Secretion To obtain the secretion of the α globin chain, the sequence encoding the signal peptide of sweet potato sporamine A was fused with the first codon of the mature α globin chain while maintaining the open reading frame. The cleaving sequence between the sequences of the signal peptide and the mature α globin chain is Ser-Val.

The sequence encoding the signal peptide (SP) of the sporamine A of the tuberized roots of sweet potato was amplified by PCR on the plasmid pMAT103 with the aid of 2 oligodeoxynucleotides, WD25 (5' cgcaagcttaaca ATG AAA GCC TTC ACA CTC GC 3'; SEQ ID NO: 20) and WD26 (5' tagaattC GGC cGG AGA CAG CAC GGA ATG GGC TGG ATT GGG CAG G 3'; SEQ ID NO: 21). The WD25 primer provides the HindIII restriction site, the aaca sequence promoting the initiation of translation (Joshi, 1987) and the first 6 codons of the signal peptide (including the initiator ATG). The WD26 primer provides the EcoRI restriction site, the first 5 codons of the sequence encoding the mature α globin chain (an EagI restriction site is created by silent mutation in the fourth codon (CCT modified to CCg)) and the last 7 codons of the sequence of the signal peptide. The PCR amplification and the treatment of the amplified DNA fragments were carried out as described in the third stage of section II.a. Next, these DNA fragments were doubly digested with HindIII and EagI, purified by electrophoresis on a 1.8% agarose gel and by the action of the "GENECLEAN™ II" kit (BIO101) and cloned at the HindIII and EagI sites of the dephosphorylated plasmid pBIOC44 described in section II.a. The ligation and the transformation were carried out as described in section I.b. The plasmid DNA of the clones obtained, selected on 100 μg/ml ampicillin, was extracted according to the alkaline lysis method (Stephen et al., 1990) and analyzed by enzymatic digestion. The resulting clone was called pBIOC60. The nucleotide sequence of this chimeric gene resulting from the translational fusion between the sequence encoding the signal peptide and the cDNA encoding the mature α globin chain was verified by sequencing as described in section I.b.

b. Construction of the Plasmid pBIOC61 Containing the cDNA Encoding the β Globin for Secretion To obtain the secretion of the β globin chain, the sequence encoding the signal peptide of the sweet potato sporamine A was fused with the first codon of the mature β globin chain while maintaining the open reading frame. The cleaving sequence between the sequences of the signal peptide and the mature β globin chain is Ser-Val.

The sequence encoding the signal peptide (SP) of the sporamine A of the tuberized roots of sweet potato was amplified by PCR on the plasmid pMAT103 with the aid of the 2 oligodeoxynucleotides, WD27 (5' gtcattaattaaca ATG AAA GCC TTC ACA CTC GC 3'; SEQ ID NO: 22) and WD28 (5' aatgagct C GGC cGA CTT CTC CTC AGG AGT CAG GTG CAC GGA ATG GGC TGG ATT GGG CAG G 3'; SEQ ID NO. 23). The WD27 primer provides the PacI restriction site, the aaca sequence promoting the initiation of translation (Joshi, 1987) and the first 6 codons of the signal peptide (including the initiator ATG). The WD28 primer provides the SacI restriction site, the first 10 codons of the sequence encoding the mature β globin chain (an EagI site is created by silent mutation in the ninth codon (TCT modified to TCg)) and the last 7 codons of the sequence of the signal peptide. The PCR amplification and the treatment of the amplified DNA fragments were carried out as described in the third stage of section II.a. Next, these DNA fragments were doubly digested with PacI and EagI, purified by electrophoresis on a 1.8% agarose gel and by the action of the "GENECLEAN™ II" kit (BIO101) and cloned at the PacI and EagI sites of the dephosphorylated plasmid pBIOC45 described in section II.b. The ligation and the transformation were carried out as described in section I.b. The plasmid DNA of the clones obtained, selected on 100 μg/ml ampicillin, was extracted according to the alkaline lysis method (Stephen et al., 1990) and analyzed by enzymatic digestion. The resulting clone was called pBIOC61. The nucleotide sequence of this chimeric gene resulting from the translational fusion between the sequence encoding the signal peptide and the cDNA encoding the mature β globin chain was verified by sequencing as described in section I.b.

c. Construction of the Co-Expression Binary Plasmid pBIOC63 Containing the cDNAs Encoding the α and β Globins for Secretion The HindIII-EcoRI fragment carrying the cDNA encoding the α globin chain for secretion was isolated from pBIOC60 described in section V.a., and ligated to the plasmid DNA of pBIOC43 doubly digested with HindIII and EcoRI, and dephosphorylated as described in II.a. The ligation and the transformation were carried out as described in section II.c.3 using the *E.coli* Sure tet_ strain. The plasmid DNA of the clones obtained, selected on 10 μg/ml tetracycline, was extracted according to the alkaline lysis method (Stephen et al., 1990) and analyzed by enzymatic digestion. The resulting clone was called pBIOC62.

The PacI-MluI fragment carrying the cDNA encoding the β globin chain for secretion was isolated from pBIOC61 described in section V.b., and ligated to the plasmid DNA of pBIOC62 doubly digested with PacI and MluI, and dephosphorylated as described in II.a. The ligation and the transformation were carried out as described in section I.b. The plasmid DNA of the clones obtained, selected on 10 μg/ml tetracyclin, was extracted according to the alkaline lysis method (Stephen et al., 1990) and analyzed by enzymatic digestion. The resulting clone was called pBIOC63.

The nucleotide sequence of the cDNAs encoding the α and β globin chains for secretion was verified by sequencing as described in section I.b. The plasmid DNA of the binary vector pBIOC63 was introduced by direct transformation into the *Agrobacterium tumefaciens* LBA4404 strain according to the method of Holsters et al. (1978). The validity of the clone selected was verified by enzymatic digestion of the plasmid DNA introduced.

VI. Construction of the Chimeric Genes Encoding the α and β Globin Chains Allowing Expression of Recombinant Human Hemoglobin in the Endoplasmic Reticulum of Tobacco Leaves The sequence encoding the KDEL signal (Lys-Asp-Glu-Leu), placed at the C-terminal end of the α and β globin chains upstream of the stop codon combined with the presence of the sequence encoding the N-terminal signal peptide (SP) of sporamine A of the tuberized roots of sweet potato allows targeting in the endoplasmic reticulum.

a. Construction of the Plasmid pBIOC65 Containing the cDNA Encoding the α Globin Allowing Retention in the Endoplasmic Reticulum To obtain retention in the endoplasmic reticulum, the sequence encoding the KDEL signal (5' aaa gat gag cta 3'; SEQ ID NO: 24) was placed before the first stop codon (TGA) of the mature α globin chain while maintaining the open reading frame.

The plasmid containing the cDNA encoding the α goblin chain which contains the sequence encoding the KDEL signal placed before its first stop codon was obtained by following the same steps as for the manufacture of the plasmid pBIOC44 described in II.a. except that the WD29 primer (5' gcgaattc TCA tag ctc atc ttt ACG GTA TTT GGA GGT CAG CAC 3'; SEQ ID NO: 25) replaces the WD14 primer. The WD29 primer provides the EcoRI restriction site and the KDEL sequence situated respectively after and before the stop codon.

The resulting plasmid obtained was called pBIOC64. The nucleotide sequence of the chimeric gene between the cDNA encoding the α globin chain and the sequence encoding of the α KDEL signal was verified by sequencing as described in section I.b.

Next, the plasmid pBIOC64 was modified as described in V.a. by translational fusion with the signal peptide of sporamine A of the tuberized roots of sweet potato to give the plasmid pBIOC65 allowing targeting in the endoplasmic reticulum. The nucleotide sequence of the chimeric gene between the sequence encoding the signal peptide, the cDNA encoding the mature α globin chain and the sequence encoding the KDEL signal was verified by sequencing as described in section I.b. The cleaving sequence between the sequences of the signal peptide and the mature α globin chain is Ser-Val.

b. Construction of the Plasmid pBIOC67 Containing the cDNA Encoding the β Globin Allowing Retention in the Endoplasmic Reticulum To obtain retention in the endoplasmic reticulum, the sequence encoding the KDEL signal (5' aaa gat gag cta 3'; SEQ ID NO: 24) was placed before the first stop codon (TAA) of the mature β globin chain while maintaining the open reading frame.

The plasmid containing the cDNA encoding the β globin chain which contains the sequence encoding the KDEL signal before its first stop codon was obtained by following the same steps as for the manufacture of the plasmid pBIOC45 described in II.b., except that the WD30 primer (5'aatgagctcgttaacgcgt TTA tag ctc atc ttt GTG ATA CTT GTG GGC CAG GGC 3'; SEQ ID NO: 26) replaces the WD16 primer. The WD30 primer provides the MluI, HpaI and SacI restriction sites and the KDEL sequence placed respectively after and before the stop codon.

The resulting plasmid obtained was called pBIOC66. The nucleotide sequence of the chimeric gene between the cDNA encoding the β globin chain and the sequence encoding the KDEL signal was verified by sequencing as described in section I.b.

Next, the plasmid pBIOC66 was modified as described in V.b. by translational fusion with the signal peptide of the sporamine A of the tuberized roots of sweet potato to give the plasmid pBIOC67 allowing targeting in the endoplasmic reticulum. The nucleotide sequence of the chimeric gene between the sequence encoding the signal peptide, the cDNA encoding the mature β globin chain and the sequence encoding the KDEL signal was verified by sequencing as described in section I.b. The cleaving sequence between the sequences of the signal peptide and the mature β globin chain is Ser-Val.

c. Construction of the Co-Expression Binary Plasmid pBIOC69 Containing the cDNAs Encoding the α and β Globins Allowing Retention in the Endoplasmic Reticulum The HindIII-EcoRI fragment carrying the cDNA encoding the α globin chain allowing retention in the endoplasmic reticulum was isolated from pBIOC65 described in section VI.a., and ligated to the plasmid DNA of pBIOC43 doubly digested with HindIII and EcoRI, and dephosphorylated as described in II.a. The ligation and the transformation were carried out as described in section I.b. The plasmid DNA of the clones obtained, selected on 10 μg/ml tetracyclin, was extracted according to the alkaline lysis method (Stephen et al., 1990) and analyzed by enzymatic digestion. The resulting clone was called pBIOC68.

The PacI-MluI fragment carrying the cDNA encoding the β globin chain allowing retention in the endoplasmic reticulum was isolated from pBIOC67 described in section VI.b., and ligated to the plasmid DNA of pBIOC68 doubly digested with PacI and MluI, and dephosphorylated as described in II.a. The ligation and the transformation were carried out as described in section II.c.3 using the *E. coli* Sure tet⁻ strain. The plasmid DNA of the clones obtained, selected on 10 μg/ml tetracyclin, was extracted according to the alkaline lysis method (Stephen et al., 1990) and analyzed by enzymatic digestion. The resulting clone was called pBIOC69.

The nucleotide sequence of the cDNAs encoding the α and β globin chains allowing their retention in the endoplasmic reticulum was verified by sequencing as described in section I.b. The plasmid DNA of the binary vector pBIOC69 was introduced by direct transformation into the *Agrobacterium tumefaciens* LBA4404 strain according to the method of Holsters et al. (1978). The validity of the clone selected was verified by enzymatic digestion of the plasmid DNA introduced.

VII. Construction of the Chimeric Genes Encoding the α and β Globin Chains Allowing Expression of the Recombinant Human Hemoglobin in the Vacuoles of Tobacco Leaves To allow vacuolar targeting, the sequence encoding the prepropeptide (PPS) of sporamine A of the tuberized roots of sweet potato (Murakami et al., 1986; Matsuoka and Nakamura, 1991), which corresponds to the signal peptide followed by the N-terminal sequence for vacuolar targeting (ATG AAA GCC TTC ACA CTC GCT CTC TTC TTA GCT CTT TCC CTC TAT CTC CTG CCC AAT CCA GCC CAT TCC AGG TTC AAT CCC ATC CGC CTC CCC ACC ACA CAC GAA CCC GCC; SEQ ID NO: 27), is fused with the first codon of the sequence encoding, on the one hand, the mature α globin chain (deletion of the initiator ATG) and, on the other hand, the mature β globin chain (deletion of the initiator ATG) while maintaining the open reading frames. This prepropeptide of 37 amino acids was isolated from the plasmid pMAT103 (Matuoka and Nakamura, 1991) and used during the carrying out of the constructions.

To obtain vacuolar targeting of the α globin chain, the sequence encoding the prepropeptide of sweet potato sporamine A was fused with the first codon of the mature α globin chain while maintaining the open reading frame. The cleaving sequence between the sequences of the signal peptide and the mature α globin chain is Ala-Val.

a. Construction of the Plasmid pBIOC70 Containing the cDNA Encoding the α Globin Allowing Vacuolar Targeting The sequence encoding the N-terminal prepropeptide (PPS) of the sporamine A of the tuberized roots of sweet potato was amplified by PCR on the plasmid pMAT103 with the aid of the 2 oligodeoxynucleotides, WD25 (5' cgcaagcttaaca ATG AAA GCC TTC ACA CTC GC 3'; SEQ ID NO: 20) described in V.a. and WD31 (5' tagaattC GGC cGG AGA CAG CAC GGC GGG TTC GTG TGT GGT TG 3'; SEQ ID NO: 28). ). The WD31 primer provides the EcoRI restriction site, the first 5 codons of the sequence encoding the mature α globin chain (an EagI site is created by silent mutation in the fourth codon (CCT modified to CCg)) and the last 6 codons of the sequence of the N-terminal prepropeptide. The PCR amplification and the treatment of the amplified DNA fragments were carried out as described in the third stage of section II.a. Next, these DNA fragments were doubly digested with HindIII and EagI, purified by electrophoresis on a 1.8% agarose gel and by the action of the "GENECLEAN™ II" kit (BIO101) and cloned at the HindIII and EagI sites of the dephosphorylated plasmid pBIOC44 described in II.a. The ligation and the transformation were carried out as described in section I.b. The plasmid DNA of the clones obtained, selected on 100 μg/ml ampicillin, was extracted according to the alkaline lysis method (Stephen et al., 1990) and analyzed by enzymatic digestion. The resulting clone was called pBIOC70. The nucleotide sequence of the chimeric gene between the sequence encoding the prepropeptide and the cDNA encoding the mature α globin chain was verified by sequencing as described in section I.b.

b. Construction of the Plasmid pBIOC71 Containing the cDNA Encoding β Globin Allowing Vacuolar Targeting To obtain vacuolar targeting of the β globin chain, the sequence encoding the prepropeptide of sporamine A of sweet potato was fused with the first codon of the mature β globin chain while maintaining the open reading frame. The cleaving sequence between the sequences of the signal peptide and the mature β globin chain is Ala-Val.

The sequence encoding the N-terminal prepropeptide (PPS) of sporamine A of the tuberized roots of sweet potato was amplified by PCR on the plasmid pMAT103 with the aid of the 2 oligodeoxynucleotides, WD27 (5' gtcattaattaaca ATG AAA GCC TTC ACA CTC GC 3'; SEQ ID NO: 22) described in V.b. and WD32 (5' aatgagct C GGC cGA CTT CTC CTC AGG AGT CAG GTG CAC GGC GGG TTC GTG TGT GGT TG 3'; SEQ ID NO: 29). The WD32 primer provides the SacI restriction site, the first 10 codons of the sequence encoding the mature β globin chain (an EagI restriction site is created by silent mutation in the ninth codon (TCT modified to TCg)) and the last 6 codons of the sequence of the N-terminal prepropeptide. The PCR amplification and the treatment of the amplified DNA fragments were carried out as described in the third stage of section II.a. Next, these DNA fragments were doubly digested with PacI and EagI, purified by electrophoresis on a 1.8% agarose gel and by the action of the "GENECLEAN™ II" kit (BIO101) and cloned at the PacI and EagI sites of the dephosphorylated plasmid pBIOC45 described in section II.b. The ligation and the transformation were carried out as described in section I.b. The plasmid DNA of the clones obtained, selected on 100 μg/ml ampicillin, was extracted according to the alkaline lysis method (Stephen et al., 1990) and analyzed by enzymatic digestion. The resulting clone was called pBIOC71. The nucleotide sequence of the chimeric gene between the sequence encoding the prepropeptide and the cDNA encoding the mature β globin chain was verified by sequencing as described in section I.b.

c. Construction of the Co-Expression Binary Plasmid pBIOC73 Containing the cDNAs Encoding the α and β Globins Allowing Vacuolar Targeting The HindIII-EcoRI fragment carrying the cDNA encoding the vacuolar targeting α globin chain was isolated from pBIOC70 described in section VII.a., and ligated to the plasmid DNA of pBIOC43 doubly digested with HindIII and EcoRI, and dephosphorylated as described in II.a. The ligation and the transformation were carried out as described in section I.b. The plasmid DNA of the clones obtained, selected on 10 μg/ml tetracyclin, was extracted according to the alkaline lysis method (Stephen et al., 1990) and analyzed by enzymatic digestion. The resulting clone was called pBIOC72.

The PacI-MluI fragment carrying the cDNA encoding the vacuolar targeting β globin chain was isolated from pBIOC71 described in section VII.b., and ligated to the plasmid DNA of pBIOC72 doubly digested with PacI and MluI, and dephosphorylated as described in II.a. The ligation and the transformation were carried out as described in section II.c.3. using the *E. coli* Sure tet⁻ strain. The plasmid DNA of the clones obtained, selected on 10 μg/ml tetracycline, was extracted according to the alkaline lysis method (Stephen et al., 1990) and analyzed by enzymatic digestion. The resulting clone was called pBIOC73.

The nucleotide sequence of the cDNAs encoding the vacuolar targeting α and β globin chains was verified by sequencing as described in section I.b. The plasmid DNA of the binary vector pBIOC73 was introduced by direct transformation into the *Agrobacterium tumefaciens* LBA4404 strain according to the method of Holsters et al. (1978). The validity of the clone selected was verified by enzymatic digestion of the plasmid DNA introduced.

VIII. Production of Transgenic Tobacco Plants

The tobacco plants used for the transformation experiments (*Nicotiana tabacum* var. PBD6) are cultured in vitro on Murashige and Skoog basic medium (1962) supplemented with Gamborg et al. vitamins (1968, Sigma reference M0404), sucrose at 20 g/l and agar (Merck) at 8 g/l. The pH of the medium is adjusted to 5.8 with a solution of potassium hydroxide before autoclaving at 120° C. for 20 min. The tobacco plantlets are transplanted by taking internode cuttings every 30 days on this MS20 propagation medium.

All the in vitro cultures are carried out in an air-conditioned chamber under the conditions defined below:

Light intensity of 30 μE.m$^{-2}$.S$^{-1}$; photoperiod of 16 h;

Thermoperiod of 26° C. by day, 24° C. by night.

The transformation technique used is derived from that of Horsch et al. (1985).

A preculture of *Agrobacterium tumefaciens* LBA4404 strain containing the plasmids pBIOC46 or pBIOC47 or pBIOC49 or pBIOC53 or pBIOC59 is carried out for 48 h at 28° C., with stirring, in LB medium supplemented with appropriate antibiotics (rifampicin and tetracycline). The preculture is then diluted 50-fold in the same medium and cultured under the same conditions. After one night, the culture is centrifuged (10 min, 3000 g), the bacteria are taken up in an equivalent volume of liquid MS30 medium (30 g/l sucrose) and this suspension is diluted 10-fold.

Explants of about 1 cm$^2$ are cut from the leaves of the plantlets described above. They are then brought into contact with the bacterial suspension for 1 h, and then dried rapidly on filter paper and placed on a coculture medium (solid MS30).

After 2 days, the explants are transferred to Petri dishes on MS30 regeneration medium containing a selective agent, kanamycin (200 mg/l), a bacteriostatic, augmentin (400 mg/l) and the hormones necessary for the induction of buds (BAP, 1 mg/l and NAA, 0.1 mg/l). A transplantation of the explants is carried out on the same medium after 2 weeks of culture. After a further 2 weeks, the buds are transplanted into Petri dishes on the development medium composed of the MS20 medium supplemented with kanamycin and augmentin. After 15 days, the buds are transplanted into pots on the same medium whose kanamycin concentration has been decreased by one half. The rooting takes about 20 days, at the end of which the plantlets can be cloned using internode cuttings in vitro or taken out to the greenhouse.

IX: Partial Extraction and Partial Purification of Recombinant Proteins From Tobacco Leaves Fifty grams of transformed tobacco leaves (fresh weight) are ground in liquid nitrogen and then left stirring for 15 min at 4° C. in 300 ml of 50 mM tris-HCl buffer pH 8 supplemented with 1 mM EDTA, 1 mM β-mercaptoethanol and polyvinylpyrrolidone (PVP, 10 g/300 ml). The ground product is filtered on miracloth and then centrifuged for 20 min at 4° C. at 10000 g. The supernatant is again filtered on miracloth. The proteins are then precipitated for 12 h at 4° C. with a solution of ammonium sulfate at saturation. After centrifuging for 20 min at 10000 g, the pellet is taken up in 50 mM tris-HCl buffer pH 8 supplemented with 1 mM DTT and 1 mM EDTA and dialyzed twice 12 hours against this same buffer. After dialysis, the retentate is centrifuged and then filtered on miracloth. An assay of proteins is also carried out according to the Bradford technique (1976).

First purification step: Equilibration in 10 mM phosphate buffer pH 6.7-1 mM EDTA by passing over a Sephadex G25 resin and then loading onto an ion-exchange resin (CM cellulose) equilibrated in 10 mM phosphate buffer ph 6.7, 1 mM EDTA. Washing with 4 volumes of this same buffer and then eluting with a linear gradient from 10 mM $Na_2HPO_4$ pH 6.7, 1 mM EDTA to 100 mM $Na_2HPO_4$ pH 6.7, 1 mM EDTA.

Second purification step: Equilibration in 10 mM Tris-HCl buffer pH 8.4-1 mM EDTA by passing over a Sephadex G25 resin and then loading onto an ion-exchange resin DEAE-Sephacel equilibrated in 10 mM Tris-HCl buffer pH 8.4, 1 mM EDTA. Washing with 4 volumes of this same buffer and then eluting with a 20 mM $KH_2PO_2$ buffer pH 7.4. The pH and ionic strength conditions can be modified according to the nature of the hemoglobin variant.

Detection of Hemoglobin

Hemoglobin (Hb) is detected by virtue of its chromophore, heme, which gives it its characteristic color. At low concentration and in the presence of another chromophore or molecule which scatters light, the signal due to Hb may be masked. This problem can be overcome using a dynamic technique which makes it possible to detect the presence of Hb in a complex system.

This method is based on differential spectra corresponding to a transition between two forms of Hb and on the photodissociation properties of ligands such as $O_2$ and CO (Gibson, 1956; Mardenet et al., 1994). The probability of dissociation being higher for CO, this ligand is therefore preferably used. The preparation of the samples is carried out under anaerobic conditions.

The experimental equipment is composed of two sources of light: the first is a pulsed source (laser) which dissociates the ligands, and the second is a continuous lamp which makes it possible to observe the recombination of the ligands by virtue of a change in the intensity of light transmitted (FIGS. 4, 5 and 6). The photodissociation is efficient in the entire visible spectral domain; our system consists of a YAG laser whose pulses have a duration of 10 ns at 532 mm. The detection is more sensitive in the Soret band (416 nm); we chose 436 nm close to the maximum absorption of the deoxy form. The changes in transmitted intensity occur first of all in a time of the order of the nanosecond (geminate phase) and then continue in a few milliseconds (bimolecular phase). We are particularly interested in this second phase which reflects the allosteric transitions of Hb (FIGS. 5 and 6). Rapid and reversible kinetic studies make it possible to obtain numerous data and therefore a reliable indication of the state of Hb as regards its normal, physiological function.

The preparation of the samples is carried out as described below. The tobacco leaves (20 g) are ground in liquid nitrogen and then the ground product is mixed with 60 ml of the extraction solution (25 mM Tris-HCl pH 7.5, 10 mM β-mercaptoethanol, 1 mM EDTA). The homogenate is centrifuged at 10000 g at 4° C. for 15 minutes. The supernatant containing the soluble proteins is collected. The assay of the proteins is carried out according to the Bradford technique (1976). To 1 ml of plant protein extract (1 mg/ml) are added 32 μl and 3.2 μl of a concentrated human hemoglobin solution (3.13 mg/ml) in order to obtain solutions containing 100%, 10% and 1% hemoglobin, respectively, relative to the total proteins.

The results obtained are the following:

The kinetics of the samples equilibrated under 0.1 atm CO for three Hb concentrations: 100%, 10% and 1% of the total proteins present in the extract in an amount of 1 mg/ml were measured. The curves are biphasic, similar to those of Hb alone, and exhibit a normal speed (of the order of 1000/s) for the rapid phase (FIG. 5). The kinetics are similar for the two concentrations, with the exception of the increase in noise (signal) predictable at low concentration. No signal was observed for the plant extract in the absence of Hb, under the same conditions. We can conclude that the kinetics of recombination of CO with HbA in an extract of tobacco leaves is normal.

X. Extraction and Partial Purification of Recombinant Hemoglobin From Tobacco Seeds In this section, the techniques used for the detection by Western blotting, the extraction and partial purification and the demonstration of the functionality of the recombinant hemoglobin produced in the seeds of transgenic tobacco plants (rHb), are described. The latter are obtained by transformation of the coexpression plasmid pBIOC 59 containing the cDNAs encoding the α and β globins allowing targeting in the chloroplast.

a. Western-Blot Detection of the Recombinant Hemoglobin Accumulated in Tobacco Seeds Seventy-five milligrams of tobacco seeds (fresh weight) are ground in liquid nitrogen and then in 600 μl of 25 mM ice-cold Tris-HCl buffer pH 8 supplemented with 1 mM EDTA, 1 mM DTT and 1 mM PMSF. The ground product is transferred into an Eppendorf tube and centrifuged at 4° C. at 10000 g for 10 min. The supernatant is then concentrated by ultrafiltration with the aid of the micropure 0.45 and microcon 10 devices (Amicon). The assay of the proteins is carried out according to the Bradford technique (1976) using bovine serum albumin (fraction V) as standard.

The proteins are separated according to their apparent molecular mass by polyacrylamide gel electrophoresis in the presence of SDS according to the Laemmli method (Laemmli, 1970) under reducing conditions. The apparatus used is the Mini-protean II (Bio-Rad). The gel consists of a concentration gel (5% acrylamide, 0.17% bis-acrylamide, 63 mM Tris-HCl pH 6.8, 0.1% SDS) and a separating gel (17% acrylamide) 0.56% bis-acrylamide, 375 mM Tris-HCl pH 8.8, 0.1% SDS). The protein samples are previously diluted with 0.25 volume of loading solution (200 mM Tris-HCl pH 6.8, 400 mM DTT, 40% glycerol, 8% SDS, 0.2% bromophenol blue), then treated at 100° C. for 5 min and finally loaded onto the gel. The electrophoresis is carried out in Tris-glycine-SDS buffer (25 mM Tris, 250 mM glycine, 1% SDS) at 25 mA.

After electrophoresis, the proteins are transferred onto a nitrocellulose membrane (BA 85, Schleicher & Schuell) by electrotransfer according to the Towbin et al. technique (1979). The transfer is carried out with the aid of the "mini trans blot module" apparatus (Bio-Rad) at 150 V for 90 min in the presence of the transfer solution (25 mM Tris, 192 mM glycine, 20% methanol). The membrane is rinsed for 5 min at room temperature in 1× PBS (10.4 mM $Na_2HPO_4$, 3.2 mM $KH_2PO_4$, 116 mM NaCl) buffer and then dried.

The presence of the globin chains on the Western-blots is detected using, as primary antibody, a rabbit anti-human hemoglobin immune serum (ref: H-4890, Sigma) and, as secondary antibody, an anti-rabbit IgG monoclonal antibody coupled to alkaline phosphatase (A-8025, Sigma). The revealing is performed using the chromogenic substrate [5-bromo-4-chloro-3-indoyl phosphate/nitro blue tetrazolium (BCIP/NBT)].

The membrane is incubated, with stirring, for 5 min in a TBST buffer solution (10 mM Tris-HCl pH 7.5, 150 mM NaCl, 0.05% Tween 20), and then for at least 30 min in the same solution supplemented with 5% skimmed milk powder (Régilait). The latter solution is replaced, 1/5000 of the volume of anti-hemoglobin immune serum is added and the membrane is incubated for at least 2 hours. It is rinsed 3 times 5 min with TBST solution. The incubation with the secondary antibody is carried out for 1 hour with the anti-rabbit IgG monoclonal antibody diluted 1/10000 in the TBST solution. Next, the membrane is again rinsed 3 times. The alkaline phosphatase activity is revealed by incubating the membrane in the revealing solution (100 mM Tris-HCl pH 9.5, 100 mM NaCl, 5 mM $MgCl_2$, 330 μg/ml BCIP, 165 μg/ml NBT). The reaction is stopped by rinsing with water.

FIG. 7 represents the Western-blot analysis of the protein composition of the extracts of seeds of tobacco plants transformed or otherwise with the plasmid pBIOC59. The polyclonal antibody recognizes the two normal adult hemoglobin (HbA) globin chains separated during the SDS-PAGE electrophoresis. It is observed that the protein extract of the seeds of the transgenic plant T26-22 differs from that of the control plant in the presence of two polypeptides whose apparent molecular mass is similar to that of the globin chains of HbA and which are recognized by the antibody. Furthermore, they appear to be represented in an equimolar manner. It can therefore be said that in the seeds, the transgenes encoding the fusion proteins transit peptide-α globins and transit peptide-β globin are expressed; the cleaving of the transit peptide would be correctly performed, such that the α and β globins accumulate. In the seeds of 11 plants, of the 20 tobacco plants transformed independently with the plasmid pBIOC59, the presence of the globins is detected. Expressed as equivalents of HbA, the maximum level of about 0.05% rHb relative to the total soluble proteins extracted is observed for the plant T26-22. It was possible to assess this by comparative Western-blot analysis of HbA concentration ranges in the protein extract of control plant seeds.

b. Extraction and Partial Purification of Recombinant Hemoglobin From Tobacco Seeds The partial purification was carried out using as starting material a mixture of the seeds of transgenic tobacco plants transformed with the plasmid pBIOC59 and expressing the rHb.

Fifteen grams of tobacco seeds (fresh weight) are ground in liquid nitrogen and then in 100 ml of 25 mM ice-cold Tris-HCl buffer pH 8 supplemented with 1 mM EDTA, 1 mM DTT and 1 mM PMSF. The ground product is filtered on miracloth® and then the filtrate is centrifuged at 4° C. at 10000 g for 10 min. The supernatant is first saturated with carbon monoxide (CO) and then filtered with a 0.22 μm filter and finally concentrated by ultrafiltration with the aid of centriprep 10 devices (Amicon). The concentrate is saturated with CO. Two successive chromatographic steps are carried out (4° C.) while monitoring the absorbance values at 280 nm (proteins) and 415 nm (hemoproteins). (i) The concentrate is previously filtered with a 0.22 μm filter and then loaded onto a Sephacryl-S100 column (Pharmacia) (2.1 cm×90 cm) equilibrated with buffer D (9.12 mM $Na_2HPO_4$, 20.88 mM $NaH_2PO_4$, 1 mM DTT, 1 mM EDTA, pH 6.5). The fraction containing the rHb is collected, filtered through a 0.22 μm filter and then saturated with CO and finally concentrated as above. Sixty-five percent of the proteins are removed at this stage. (ii) This concentrate is loaded onto the second column, a fast-flow S-sepharose (Pharmacia) (1.1 cm×10 cm) equilibrated with buffer D. After washing with 8 volumes of buffer D, an ionic strength gradient is applied (buffer D to buffer D containing 500 mM NaCl). The hemoglobin is eluted at one peak. The fractions containing this peak are combined and the proteins are concentrated as described above. Before and after concentrating, the samples are saturated with CO. This concentrate constitutes the rHb-enriched fraction called FE-rHb. Only 3% of the proteins of the extract now remain in this fraction. To obtain a control for subsequent analyzes, this purification scheme was applied under the same conditions to an extract obtained from 15 g of tobacco seeds not expressing rHb, leading to the production of the fraction called FE-Control.

The presence of the α and β globins in these fractions was tested for using the Western-blot technique under the conditions described in paragraph X.a. The FE-rHb fraction indeed contains rHb, these two polypeptides being detected (FIG. 8).

c. Demonstration of the Functionality of the Recombinant Hemoglobin by Flash Photolysis The demonstration of the functionality was performed using, as starting material, the rHb-enriched fraction called FE-rHb, using, as control, the equivalent control reaction FE-Control and HbA.

The control experiments where $1_F$HbA was added to the plant extract showed biphasic recombination kinetics and variations of the slow fraction depending on the energy of the flash of laser light. These results demonstrate that the function of HbA is not altered by the solvent conditions used.

After photodissociation of the ligands from Hb, bimolecular recombination occurs within a time scale of μs-ms (k-on speed). Although the natural physiological ligand is oxygen, the studies described were performed with carbon monoxide (CO) which gives a photodissociation signal which is much greater than that obtained with $O_2$ because the yield is higher. Likewise, the difference in the speeds of recombination for the two conformations of Hb (R and T corresponding to tetramers with and without ligand) is also higher. Experimentally, the samples are equilibrated under 0.1 atm CO which gives the best conditions of observation of the two phases. As the reaction is reversible, the photodissociation (γ) of the same sample can be repeated in order to accumulate several curves, which greatly improves the signal/noise ratio.

$$\text{HbCO} \underset{\text{k-on-CO}}{\overset{\gamma}{\rightleftharpoons}} \text{Hb} + \text{CO}$$

The observation of a variation of the amplitude of slow recombination as a function of the dissociation fraction (by modification of the laser energy) demonstrates the presence of a functional hemoglobin.

The transgenic plants receive genetic information only for the synthesis of globin and not for heme. Consequently, if functional Hb (globins+heme) is expressed in plants, it means that it has captured the heme in situ. Other hemoproteins present in plants give an optical signal after flash photolysis. These hemoproteins will not give a signal if the hemin iron is in the ferric form which does not bind the CO and $O_2$ ligands. CO and $O_2$ bind reversibly only if the iron atom is in the ferrous form. It is consequently important to demonstrate the existence of kinetic processes for the two phases and the variation in the relative contributions of the two phases due to factors known to influence the function of hemoglobin.

The enriched sample FE-rHb shows a CO photodissociation signal of 48 mOD (optical density) and makes it possible to carry out certain experiments at different levels of dissociation; these experiments are carried out in the absence of sodium dithionite in order to avoid any parasitic contribution due to the presence of hemoproteins. The same experiment, carried out with the FE-Control fraction showed a signal of 1 mOD (FIG. 9).

The results recorded at various levels of laser light energy are shown in FIG. 10. The curves are similar to that of HbA and shows the existence of a characteristic property of hemoglobin, namely the lower fraction of slow speed when the light intensity is decreased so as to obtain a lower dissociation.

The sample was then equilibrated under a CO atmosphere. As expected, the recombination kinetics are thereafter more rapid. For hemoglobin in solution, the slow fraction is usually lower at high CO concentration since there is less time available to make the R→T transition after dissociation. The FE-rHb sample does not exhibit this effect (FIG. 11).

Another method can be used to study the speeds of association and of dissociation of oxygen. The principle of this method is based on the following fact: although CO has an affinity about 200 times higher than that of oxygen, the speed of association of CO with the ligand-containing Hb (R state) is about 10 times lower than for oxygen. A sample equilibrated with an equal mixture of CO and $O_2$ will be essentially in the HbCO form. It is then possible to photodissociate the CO with a high yield), which allows the study of the recombination of $O_2$. A slow terminal phase of the order 1 s due to the replacement of oxygen by CO provides information on the speed of dissociation (k-off). Only the FE-rHb sample reveals a signal for binding of oxygen (FIG. 11).

The studies of the FE-rHb fraction by flash photolysis have shown:

a biphasic recombination of CO with rapid and slow speeds similar to those observed in tetrameric Hb A;

a decrease in the slow fraction at low laser energy as for Hb A;

an increase in speed for higher CO concentrations as for normal Hb;

a reversible binding of oxygen with on and off speeds similar to those of normal Hb A;

It can be concluded that the recombinant hemoglobin produced in tobacco seeds possesses the properties of tetrameric Hb A in all the functional tests carried out.

XI. Construction of Chimeric Genes Encoding the α and β Chains of Human Hemoglobin and Allowing Expression in Maize Seeds Construction of the Plasmids Containing One of the α or β Chains of Human Hemoglobin and Allowing Constitutive Expression or Expression in the Albumin in Maize Seeds The constitutive or albumin-specific expression, in maize seeds, of the sequences of the α and β chains of human hemoglobin required the following regulatory sequences: one of the three promoters allowing a constitutive expression:

rice actin promoter followed by the rice actin intron (pAR-IAR) contained in the plasmid pAct1-F4 described by McElroy et al. (1991);

35S double constitutive promoter (pd35S) of CaMV (cauliflower mosaic virus). It corresponds to a duplication of the sequences activating transcription, situated upstream of the TATA element of the natural 35S promoter (Kay et al., 1987).

the promoter of the maize γzein gene (pγzein) contained in the plasmid pγ63 (Reina et al., 1990). The plasmid pγ63 results from the cloning of pγzein at the HindIII and XbaI sites of a plasmid pUC18 containing, between its HindIII and EcoRI sites, the expression cassette "p35S-gus-tNOS" of pBI221 marketed by Clontech. It allows expression of the albumin maize seeds. Combined with the rice actin intron, this promoter confers expression is of constitutive type;

one of the two terminators:

the sequence for termination of transcription, 35S polyA terminator, which corresponds to the noncoding 3' region of the sequence of the circular double-stranded DNA cauliflower mosaic virus producing the 35S transcript (Franck et al., 1980);

The sequence for termination of transcription, NOS polyA terminator, which corresponds to the noncoding 3' region of the nopaline synthase gene of the Ti plasmid of nopaline-containing strain of *Agrobacterium tumefaciens* (Depicker et al., 1982).

The type of vector used is derived from pBSIISK+ (Stratagene). Each vector comprises an expression cassette, namely one of the promoters, one of the α or β chains of human hemoglobin and one of the terminators. Vectors comprising the two cassettes for expression of each of the α and β chains of human hemoglobin were also constructed. The clonings were carried out according to the customary methods.

Bibliographic References

Benesch & Kwong. Hemoglobin 1994, 18, 185–192.
Birnboim & Doly. Nucleic Acids Res. 1979, 7, 1513–1523.
Boutry & Chua. EMBO J. 1985, 4, 2159–2165.
Bradford. Anal. Biochem. 1976, 72, 248–254.
Carrer et al. Mol. Gen. Genet. 1993, 241, 49–56.
Chaumont et al. Plant Mol. Biol. 1994, 24, 631–641.
Gamborg et al. Exp. Cell Res. 1968, 50, 151–158.
Guerineau et al. Nucleic Acid Res. 1988, 16, 11380.
Gibson. J. Physiol. 1956, 134, 123.
Edelbaum. J. Interferon Res. 1992, 12, 449–453.
Hanahan. J. Mol. Biol. 1983, 166, 557–580.
Hanahan. In "DNA cloning volume I, a practical approach" (Ed: Glover D. M.) IRL Press, 1985, pp 109–135.
Hiatt & Ma. FEBS Let. 1992, 307, 71–75.
Hoffman et al. Proc. Natl. Acad. Sci. USA 1990, 87: 8521–8525.
Horsch et al. Science 1985, 227, 1229–1231.
International Hemoglobin Information Center (1995) Hemoglobin, 19, 37–124.
Jessen et al. Meth Enzymol, 1994, 231, 347–364.
Joshi. Nucleic Acid Res. 1987, 15, 6643–6653.
Kister et al. J. Biol. Chem. 1987, 262, 12085–12091.
Krebbers et al. Plant Physiol. 1988, 87, 859–866.
Marden et al. Meth Enzymol. 1994, 232 71–86.
Mason et al. Proc. Natl. Acad. Sci. USA 1992, 89, 11745–11749.
Moloney. Int. Meeting of Production of Recombinant Proteins in Plants, Leicester 1994, page 36–38
Murashige & Skoog. Physiol. Plantarum 1962, 15, 473–497.
Nagai & Thogersen. Meth. Enzymol. 1987, 153, 461–481.
Nagai et al. Proc. Natl. Acad. Sci. USA 1985, 82, 7252–7255.
Perutz. Nature 1970, 228, 726–739.
Russel. Int. Meeting of Production of Recombinant Proteins in Plants, Leicester 1994, page 43
Sambrook et al. Molecular Cloning: A Laboratory Manual. Second Edition. Cold Spring Harbor Laboratory Press, Cold Spring Harbor, N.Y. (1989).
Sanger et al. Proc. Natl. Acad. Sci. USA 1977, 74, 5463–51467
Stephen et al. Nucleic Acid Res. 1990, 18, 7463–7464.
Svab et al. Proc. Natl. Acad. Sci. USA 1990, 87, 8526–8530.
Swanson et al. Bio/Technology 1991, 9, 57–61.
Symons et al. Bio/Technology 1990, 8, 217–221.
Vanderkerckhove et al. Bio/Technology 1989, 7, 929–932.
Wagenbach et al. Biotechnology 1991, 9: 57–61.
Wilson et al. Nucleic Acid Res. 1978, 5, 563–581.
Kay R. et al., Science, 1987, 236: 1299.
Franck A. et al., Cell, 1980, 21: 285.
Depicker A. et al., J. Mol. Appl. Genet., 1982, 1: 561.
Mc Elroy et al., Mol. Gen. Genet., 1991, 231: 150.
Reina et al., N.A.R., 1990, 18: 6426.
Dumoulin et al., Prot. Sci., 1996, 5: 114–120.
Feng et al., J. Mol. Evol., 1985, 21: 112–115.
Dumoulin et al., Art. Cells Blood Subs. Immob. Biotech., 1994, 22: 733–738.
Looker et al., Nature, 1992, 356: 258–260.
Laemmli, Nature, 1970, 227: 680–685.
Towbin et al., Proc. Natl. Acad. Sci. USA, 1979, 76: 4350–4354.

What is claimed is:

1. A recombinant hemin protein having the capacity to reversibly bind oxygen, comprising at least one iron-containing porphyrin nucleus, of plant origin, and a protein component comprising at least one polypeptide chain selected from the group consisting on hemoglobin, myoglobin, cytochromes, peroxidases, and catalases of animal origin.

2. The recombinant protein according to claim 1, wherein the at least one iron-containing porphyrin nucleus is iron-containing protoporphyrin IX, or a protoporphyrin differing from protoporphyrin IX in the nature of the side chains, carried by the β atoms of pyrrole rings.

3. The recombinant protein according to claim 1, wherein the protein component comprises at least one α and/or β-globin polypeptide chain, or variants of said polypeptide chain, wherein the variant of the α chain has at least 90% homology with an α chain having an amino acid sequence of SEQ ID NO:31 and the variant of the β chain has at least 90% homology with a β chain having an amino acid sequence of SEQ ID NO:33, and the hemin protein is capable of binding oxygen reversibly.

4. The recombinant protein according to claim 3, wherein the α or β-globin chain, or variants of the said polypeptide chain, further comprises a chloroplast targeting signal, a mitochondrial targeting signal, or a N-terminal signal peptide in combination with a signal responsible for retaining a protein in the endoplasmic reticulum or a N-terminal signal peptide in combination with a vacuolar targeting signal.

5. The recombinant protein according to claim 3, wherein each α and/or β-globin polypeptide chain lacks an $NH_2$ terminal methionine.

6. The recombinant hemin protein according to claim 1, wherein the protein component comprises at least four polypeptide chains of α and/or β-globin or variants of the said polypeptide chain, each said polypeptide chain being bound to an iron-containing protoporphyrin nucleus, wherein the variant of the α chain has at least 90% homology with an α chain having an amino acid sequence of SEQ ID NO:31 and the variant of the β chain has at least 90% homology with a β chain having an amino acid sequence of SEQ ID NO:33, and the hemin protein is capable of binding oxygen reversibly.

7. The recombinant protein according to claim 6, wherein the protein component comprises 2 α-globin chains and 2 β globin chains, or variants of the said polypeptide chain.

8. The recombinant protein according to claim 1, wherein said protein binds oxygen with an affinity of between 7 and 40 mm Hg.

9. A pharmaceutical product comprising one or more recombinant hemin protein(s) according to claim 1 in association with a physiologically acceptable excipient.

10. A recombinant hemin protein having the capacity to reversibly bind oxygen, comprising at least one iron-containing porphyrin nucleus of plant origin, and a protein component comprising at least one polypeptide chain selected from the group consisting of hemoglobin, myoglobin, and cytochromes of animal origin.

11. The recombinant protein according to claim 10, wherein the at least one iron-containing porphyrin nucleus is iron-containing protoporphyrin IX, or a protoporphyrin differing from protoporphyrin IX in the nature of the side chains, carried by the β atoms of pyrrole rings.

12. The recombinant protein according to claim 10, wherein the protein component comprises at least one α and/or β-globin polypeptide chain, or variants of said polypeptide chain, wherein the variant of the α chain has at least 90% homology with an α chain having an amino acid sequence of SEQ ID NO:31 and the variant of the β chain has at least 90% homology with a β chain having an amino acid sequence of SEQ ID NO:33, and the hemin protein is capable of binding oxygen reversibly.

13. The recombinant protein according to claim 12, wherein the α or β-globin chain, or variants of the said polypeptide chain, further comprises a chloroplast targeting signal, a mitochondrial targeting signal, or a N-terminal signal peptide in combination with a signal responsible for retaining a protein in the endoplasmic reticulum or a N-terminal signal peptide in combination with a vacuolar targeting signal.

14. The recombinant protein according to claim 12, wherein each α and/or β-globin polypeptide chain lacks an $NH_2$ terminal methionine.

15. The recombinant hemin protein according to claim 10, wherein the protein component comprises at least four polypeptide chains of α and/or β-globin or variants of said polypeptide chain, each said polypeptide chain being bound to an iron-containing protoporphyrin nucleus, wherein the variant of the α chain has at least 90% homology with an α chain having an amino acid sequence of SEQ ID NO:31 and the variant of the β chain has at least 90% homology with a β chain having an amino acid sequence of SEQ ID NO:33, and the hemin protein is capable of binding oxygen reversibly.

16. The recombinant protein according to claim 15, wherein the protein component comprises 2 α-globin chains and 2 β chains, or variants of the said polypeptide chain.

17. The recombinant protein according to claim 10, wherein said protein binds oxygen with an affinity of between 7 and 40 mm Hg.

18. A pharmaceutical product comprising one or more recombinant hemin protein(s) according to claim 10 in association with a physiologically acceptable excipient.

19. The recombinant protein according to claim 10, wherein the protein component comprises at least one α and/or β-globin polypeptide chain, or variants of said polypeptide chain, wherein the variant of the α chain has a heme binding domain and the variant of the β chain has a heme binding domain and the hemin protein is capable of binding oxygen reversibly.

* * * * *

UNITED STATES PATENT AND TRADEMARK OFFICE
CERTIFICATE OF CORRECTION

PATENT NO. : 6,916,787 B2
DATED : July 12, 2005
INVENTOR(S) : Merot et al.

It is certified that error appears in the above-identified patent and that said Letters Patent is hereby corrected as shown below:

Title page,
Item [56], References Cited, OTHER PUBLICATIONS,
"Abler" reference, "the mazie Cat3" should read -- the maize Cat3 --.
"Maurice M. Moloney" reference, "Gus Van Rooijen" should read -- Gijs Van Rooijen --.
"Kumar" reference, "*Experimental Biotechnology and*" should read -- *Experimental Biology and* --.

Column 8,
Line 45, "and degenerate sequence" should read -- any degenerate sequence --.

Column 15,
Line 36, "*E. coli* DH5☐" should read -- *E. coli* DH5α --.
Line 46, "reaction condidtions follow" should read -- reaction conditions follow --.

Column 16,
Lines 57 and 65, "mature ☐ globin" should read -- mature α globin --.

Column 17,
Line 20, "mature ☐ globin" should read -- mature α globin --.
Line 52, "of the "Geneclean II" kit" should read -- of the "GENECLEAN$^{TM}$" kit --.
Line 64, "of the "Sequenase" should read -- of the "SEQUENASE$^{TM}$ --.

Column 19,
Lines 14-15, "pBIOC21 digested with" should read -- pBIOC21 doubly digested with --.

Column 20,
Line 42, "ATPase-F1 ☐ subunit" should read -- ATPase-F1 β subunit --.
Line 64, "0.7% agarose gel" should read -- 0.75% agarose gel --.

Column 21,
Line 25, "ATPase-F1 ☐ subunit" should read -- ATPase-F1 β subunit --.
Line 38, "in the ninth condon" should read -- in the ninth codon --.

Column 22,
Line 6, "of the cones obtained," should read -- of the clones obtained, --.

UNITED STATES PATENT AND TRADEMARK OFFICE
CERTIFICATE OF CORRECTION

PATENT NO. : 6,916,787 B2
DATED : July 12, 2005
INVENTOR(S) : Merot et al.

It is certified that error appears in the above-identified patent and that said Letters Patent is hereby corrected as shown below:

<u>Column 33,</u>
Line 52, "times 5 min" should read -- times for 5 min --.

<u>Column 38,</u>
Line 17, "5463-51467" should read -- 5463-5467 --.

Signed and Sealed this

Sixth Day of December, 2005

JON W. DUDAS
*Director of the United States Patent and Trademark Office*

SEQUENCE LISTING

<160> NUMBER OF SEQ ID NOS: 33

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic: pBIOC21

<400> SEQUENCE: 1
agctgattaa ttaaggcgcg ccacgcgtta ac                          32

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic: pBIOC21

```
<400> SEQUENCE: 2
aattgttaac gcgtggcgcg ccttaattaa tc                              32

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence:
      Homo sapiens

<400> SEQUENCE: 3
tacaagctta acaatggtgc tgtctccggc cgac                            34

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      Homo sapiens

<400> SEQUENCE: 4
cgggtccacc cggagcttgt g                                          21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:
      Homo sapiens

<400> SEQUENCE: 5
cacaagctcc gggtggaccc g                                          21

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:
      Homo sapiens

<400> SEQUENCE: 6
tcaacggtat ttggaggtca gcac                                       24

<210> SEQ ID NO 7
<211> LENGTH: 52
<212> TYPE: DNA
<213> ORGANISM: Artificial Sequence
<220> FEATURE:
<223> OTHER INFORMATION: Description of Artificial Sequence:
      Homo sapiens

<400> SEQUENCE: 7
gtcattaatt aacaatggtg cacctgactc ctgaggagaa gtcggccgtt ac         52

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence:
      Homo sapiens

<400> SEQUENCE: 8
```

```
aatgagctcg ttaacgcgtt tagtgatact tgtgggccag ggc                43
```

<210> SEQ ID NO 9
<211> LENGTH: 162
<212> TYPE: DNA
<213> ORGANISM: Nicotiana plumbaginifolia

<400> SEQUENCE: 9

```
atggcttctc ggaggcttct cgcctctctc ctccgtcaat cggctcaacg tggcggcggt    60
ctaatttccc gatcgttagg aaactccatc cctaaatccg cttcacgcgc ctcttcacgc   120
gcatccccta agggattcct cttaaaccgc gccgtacagt ac                      162
```

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Nicotiana
      plumbaginifolia

<400> SEQUENCE: 10

```
cgcaagctta acaatggctt ctcggaggct tctc                          34
```

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: Synthetic:
      Nicotiana plumbaginifolia and Homo sapiens

<400> SEQUENCE: 11

```
tagaattcgg ccggagacag cacgtactgt acggcgcggt ttaag              45
```

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Nicotiana
      plumbaginifolia

<400> SEQUENCE: 12

```
gtcattaatt aacaatggct ctcggaggc ttctcgcctc tc                  42
```

<210> SEQ ID NO 13
<211> LENGTH: 61
<212> TYPE: DNA
<213> ORGANISM: Artificial Sequence
<220> FEATURE:
<223> OTHER INFORMATION: Description of Artificial Sequence: Synthetic:
      Nicotiana plumbaginifolia and Homo sapiens

<400> SEQUENCE: 13

```
aatgagctcg gccgacttct cctcaggagt caggtgcacg tactgtacgg cgcggtttaa    60
g                                                                    61
```

<210> SEQ ID NO 14
<211> LENGTH: 171
<212> TYPE: DNA
<213> ORGANISM: Pisum sativum

<400> SEQUENCE: 14

```
atggcttcta tgatatcctc ttcagctgtg actacagtca gccgtgcttc tacggtgcaa       60
tcggccgcgg tggctccatt cggcggcctc aaatccatga ctggattccc agttaagaag      120
gtcaacactg acattacttc cattacaagc aatggtggaa gagtaaagtg c               171
```

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence:
      Pisum sativum

<400> SEQUENCE: 15

```
cgcaagctta acaatggctt ctatgatatc ctcttcagc                              39
```

<210> SEQ ID NO 16
<211> LENGTH: 46
<212> TYPE: DNA
<213> ORGANISM: Artificial Sequence
<220> FEATURE:
<223> OTHER INFORMATION: Description of Artificial Sequence:  Synthetic:
      Pisum sativum and Homo sapiens

<400> SEQUENCE: 16

```
tagaattcgg ccggagacag cacgcacttt actcttccac cattgc                      46
```

<210> SEQ ID NO 17
<211> LENGTH: 44
<212> TYPE: DNA
<213> ORGANISM: Artificial Sequence
<220> FEATURE:
<223> OTHER INFORMATION: Description of Artificial Sequence:
      Pisum sativum

<400> SEQUENCE: 17

```
gtcattaatt aacaatggct tctatgatat cctcttcagc tgtg                        44
```

<210> SEQ ID NO 18
<211> LENGTH: 57
<212> TYPE: DNA
<213> ORGANISM: Artificial Sequence
<220> FEATURE:
<223> OTHER INFORMATION: Description of Artificial Sequence:  Synthetic:
      Pisum sativum and Homo sapiens

<400> SEQUENCE: 18

```
aatgagctcg gccgacttct cctcaggagt caggtgcacg cactttactc ttccacc          57
```

<210> SEQ ID NO 19
<211> LENGTH: 69
<212> TYPE: DNA
<213> ORGANISM: Ipomoea batatas

<400> SEQUENCE: 19

```
atgaaagcct tcacactcgc tctcttctta gctctttccc tctatctcct gcccaatcca       60
gcccattcc                                                               69
```

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence:  Ipomoea
      batatas

```
<400> SEQUENCE: 20
cgcaagctta acaatgaaag ccttcacact cgc                                  33

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence:  Synthetic:
      Ipomoea batatas and Homo sapiens

<400> SEQUENCE: 21
tagaattcgg ccggagacag cacggaatgg gctggattgg gcagg                     45

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence:  Ipomoea
      batatas

<400> SEQUENCE: 22
gtcattaatt aacaatgaaa gccttcacac tcgc                                 34

<210> SEQ ID NO 23
<211> LENGTH: 61
<212> TYPE: DNA
<213> ORGANISM: Artificial Sequence
<220> FEATURE:
<223> OTHER INFORMATION: Description of Artificial Sequence:  Synthetic:
      Ipomoea batatas and Homo sapiens

<400> SEQUENCE: 23
aatgagctcg gccgacttct cctcaggagt caggtgcacg gaatgggctg gattgggcag     60
g                                                                    61

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence:
      Homo sapiens

<400> SEQUENCE: 24
aaagatgagc ta                                                         12

<210> SEQ ID NO 25
<211> LENGTH: 44
<212> TYPE: DNA
<213> ORGANISM: Artificial Sequence
<220> FEATURE:
<223> OTHER INFORMATION: Description of Artificial Sequence:
      Homo sapiens

<400> SEQUENCE: 25
gcgaattctc atagctcatc tttacggtat ttggaggtca gcac                      44

<210> SEQ ID NO 26
<211> LENGTH: 55
<212> TYPE: DNA
<213> ORGANISM: Artificial Sequence
<220> FEATURE:
<223> OTHER INFORMATION: Description of Artificial Sequence:
      Homo sapiens
```

<400> SEQUENCE: 26
aatgagctcg ttaacgcgtt tatagctcat ctttgtgata cttgtgggcc agggc         55

<210> SEQ ID NO 27
<211> LENGTH: 111
<212> TYPE: DNA
<213> ORGANISM: Ipomoea batatas

<400> SEQUENCE: 27
atgaaagcct tcacactcgc tctcttctta gctctttccc tctatctcct gcccaatcca    60
gcccattcca ggttcaatcc catccgcctc cccaccacac acgaacccgc c             111

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Synthetic:
      Ipomea batatas and Homo sapiens

<400> SEQUENCE: 28
tagaattcgg ccggagacag cacggcgggt tcgtgtgtgg ttg                      43

<210> SEQ ID NO 29
<211> LENGTH: 59
<212> TYPE: DNA
<213> ORGANISM: Artificial Sequence
<220> FEATURE:
<223> OTHER INFORMATION: Description of Artificial Sequence: Synthetic:
      Ipomea batatas and Homo sapiens

<400> SEQUENCE: 29
aatgagctcg gccgacttct cctcaggagt caggtgcacg gcgggttcgt gtgtggttg     59

<210> SEQ ID NO 30
<211> LENGTH: 423
<212> TYPE: DNA
<213> ORGANISM: Homo sapiens

<400> SEQUENCE: 30
gtgctgtctc ctgccgacaa gaccaacgtc aaggccgcct ggggcaaggt tggcgcgcac    60
gctggcgagt atggtgcgga ggccctggag aggatgttcc tgtccttccc caccaccaag   120
acctacttcc cgcacttcga cctgagccac ggctctgccc aggttaaggg ccacggcaag   180
aaggtggccg acgcgctgac caacgccgtg gcgcacgtgg acgacatgcc caacgcgctg   240
tccgccctga gcgacctgca cgcgcacaag cttcgggtgg acccggtcaa cttcaagctc   300
ctaagccact gcctgctggt gaccctggcc gcccacctcc ccgccgagtt caccccctgcg   360 gtgcacgcct ccctggacaa gttcctggct tctgtgagca ccgtgctgac ctccaaatac   420
cgt                                                                423

<210> SEQ ID NO 31
<211> LENGTH: 141
<212> TYPE: PRT
<213> ORGANISM: Homo sapiens

<400> SEQUENCE: 31

Val Leu Ser Pro Ala Asp Lys Thr Asn Val Lys Ala Ala Trp Gly Lys
 1               5                  10                  15

Val Gly Ala His Ala Gly Glu Tyr Gly Ala Glu Ala Leu Glu Arg Met

```
                   20                  25                  30
Phe Leu Ser Phe Pro Thr Thr Lys Thr Tyr Phe Pro His Phe Asp Leu
             35                  40                  45

Ser His Gly Ser Ala Gln Val Lys Gly His Gly Lys Lys Val Ala Asp
         50                  55                  60

Ala Leu Thr Asn Ala Val Ala His Val Asp Asp Met Pro Asn Ala Leu
 65                  70                  75                  80

Ser Ala Leu Ser Asp Leu His Ala His Lys Leu Arg Val Asp Pro Val
                 85                  90                  95

Asn Phe Lys Leu Leu Ser His Cys Leu Leu Val Thr Leu Ala Ala His
                100                 105                 110

Leu Pro Ala Glu Phe Thr Pro Ala Val His Ala Ser Leu Asp Lys Phe
            115                 120                 125

Leu Ala Ser Val Ser Thr Val Leu Thr Ser Lys Tyr Arg
        130                 135                 140

<210> SEQ ID NO 32
<211> LENGTH: 438
<212> TYPE: DNA
<213> ORGANISM: Homo sapiens

<400> SEQUENCE: 32
gtgcacctga ctcctgagga aagtctgcc gttactgccc tgtggggcaa ggtgaacgtg      60
gatgaagttg gtggtgaggc cctgggcagg ctgctggttg tctacccttg acccagagg    120 ttctttgagt ccttttgggga tctgtccact cctgatgctg ttatgggcaa ccctaaggtg    180
aaggctcatg gcaagaaagt gctcggtgcc tttagtgatg gcctggctca cctggacaac    240
ctcaagggca cctttgccac actgagtgag ctgcactgtg acaagctgca cgtggatcct    300
gagaacttca ggctcctggg caacgtgctg gtctgtgtgc tggcccatca ctttggcaaa    360
gaattcaccc caccagtgca ggctgcctat cagaaagtgg tgctggtgt ggctaatgcc    420 ctagcccaca agtatcac                                                  438

<210> SEQ ID NO 33
<211> LENGTH: 146
<212> TYPE: PRT
<213> ORGANISM: Homo sapiens

<400> SEQUENCE: 33

Val His Leu Thr Pro Glu Glu Lys Ser Ala Val Thr Ala Leu Trp Gly
  1               5                  10                  15

Lys Val Asn Val Asp Glu Val Gly Gly Glu Ala Leu Gly Arg Leu Leu
             20                  25                  30

Val Val Tyr Pro Trp Thr Gln Arg Phe Phe Glu Ser Phe Gly Asp Leu
         35                  40                  45

Ser Thr Pro Asp Ala Val Met Gly Asn Pro Lys Val Lys Ala His Gly
     50                  55                  60

Lys Lys Val Leu Gly Ala Phe Ser Asp Gly Leu Ala His Leu Asp Asn
 65                  70                  75                  80

Leu Lys Gly Thr Phe Ala Thr Leu Ser Glu Leu His Cys Asp Lys Leu
                 85                  90                  95

His Val Asp Pro Glu Asn Phe Arg Leu Leu Gly Asn Val Leu Val Cys
                100                 105                 110

Val Leu Ala His His Phe Gly Lys Glu Phe Thr Pro Pro Val Gln Ala
            115                 120                 125
```

```
Ala Tyr Gln Lys Val Val Ala Gly Val Ala Asn Ala Leu Ala His Lys
    130             135                 140

Tyr His
145
```